United States Patent [19]

Urry

[11] Patent Number: 5,064,430
[45] Date of Patent: Nov. 12, 1991

[54] POLYNONAPEPTIDE BIOELASTOMERS HAVING AN INCREASED ELASTIC MODULUS

[75] Inventor: Dan W. Urry, Birmingham, Ala.

[73] Assignee: UAB Research Foundation, Birmingham, Ala.

[21] Appl. No.: 314,115

[22] Filed: Feb. 23, 1989

Related U.S. Application Data

[60] Continuation-in-part of Ser. No. 13,343, Feb. 11, 1987, abandoned, which is a division of Ser. No. 793,225, Oct. 31, 1985, Pat. No. 4,693,718.

[51] Int. Cl.$^5$ .......................... A61F 2/06; A61K 37/02
[52] U.S. Cl. .......................................... 623/1; 623/11; 530/328; 530/330
[58] Field of Search ............... 623/66, 1, 11; 530/328, 530/330

[56] References Cited

U.S. PATENT DOCUMENTS 4,693,718 9/1987 Urry et al. .......................... 623/66 X
4,783,523 11/1988 Urry et al. .......................... 530/328 X

*Primary Examiner*—Alan W. Cannon
*Attorney, Agent, or Firm*—Richard L. Neeley

[57] ABSTRACT

A polynonapeptide of the formula:

—X—$(\alpha\beta\gamma\delta\epsilon\theta\lambda\pi\rho)_n$Y— wherein:
   $\alpha$ is a peptide-forming residue of L-Valine or another peptide-forming residue capable of functioning in position i of a $\beta$-turn in a polypeptide;
   $\beta$ is a peptide-forming residue of L-Proline or another peptide-forming residue capable of functioning in position i+1 of a $\beta$-turn in a polypeptide;
   $\gamma$ is a peptide-forming residue of L-Glycine or another peptide-forming residue capable of functioning in position i+2 of a $\beta$-turn in a polypeptide;
   $\delta$ is a peptide-forming residue of L-Phenylalanine or another peptide-forming residue capable of functioning in position i+3 of a $\beta$-turn in a polypeptide;
   $\epsilon$ is a peptide-forming residue of Glycine, or D-Alanine, when functioning as position i' of a subsequent $\beta$-turn in a polypeptide when $\delta$ is as defined, or $\epsilon$ is as defined for $\alpha$ when $\delta$ is Glycine or D-Alanine;
   $\theta$ is a peptide-forming residue of L-Valine, L-Alanine or another peptide-forming residue as defined above for $\alpha$, or when functioning as position (i+1)' of a subsequent $\beta$-turn in a polypeptide, $\theta$ is a peptide-forming residue as defined above for $\beta$;
   $\lambda$ is a peptide-forming residue of Glycine, D-Alanine or another peptide-forming residue as defined for $\gamma$, when functioning as position (i+2)' of a subsequent $\beta$-turn in a polypeptide;
   $\pi$ is a peptide-forming residue of L-Alanine or another peptide-forming residue as defined for $\delta$, when functioning as position (i+3)' in a subsequent $\beta$-turn in a polypeptide, or a direct bond; and
   $\rho$ is a peptide-forming residue of Glycine, or D-Alanine;
wherein X is $\beta\gamma\delta\epsilon\theta\lambda\pi\rho$, $\gamma\delta\epsilon\theta\lambda\pi\rho$, $\gamma\epsilon\theta\lambda\pi\rho$, $\epsilon\theta\lambda\pi\rho$, $\theta\lambda\pi\rho$, $\lambda\pi\rho$, $\pi\rho$, $\pi$ or a direct bond; Y is $\alpha\beta\gamma\delta\epsilon\theta\lambda\pi$, $\alpha\beta\gamma\delta\epsilon\theta\lambda$, $\alpha\beta\gamma\delta\epsilon\theta$, $\alpha\beta\gamma\delta\epsilon$, $\alpha\beta\gamma\delta$, $\alpha\beta\gamma$, $\alpha\beta$, $\alpha$ or a direct bond; and n has a value of 1 to about 5,000, and with the proviso that no more than three or residues $\epsilon$, $\theta$, $\lambda$, $\pi$ and $\rho$ are simultaneously a peptide-forming residue of Glycine.

The polynonapeptides have increased elastic moduli and exhibit chemotaxis toward fibroblasts and endothelial cells.

18 Claims, 4 Drawing Sheets

POLYNONAPEPTIDE BIOELASTOMERS HAVING AN INCREASED ELASTIC MODULUS

BACKGROUND OF THE INVENTION

The government has rights in this invention as a result of the work described herein being supported in part by the National Institutes of Health under Grant No. HL-29578.

This application is a continuation-in-part application of U.S. application Ser. No. 013,343, filed Feb. 11, 1987 now abandoned which is a divisional application of U.S. application Ser. No. 793,225, filed Oct. 31, 1985, now U.S. Pat. No. 4,693,718.

1. Field of the Invention

The present invention relates to polynonapeptide bioelastomers having an increased elastic modulus, being chemotactic peptides toward which fibroblasts and endothelial cells migrate and which are particularly suitable for constructing artificial ligaments and vascular walls.

2. Description of the Background

Bioelastomeric materials are elastomeric polypeptide biomaterials which have as their origins repeating sequences from elastin, the extracellular elastic protein of higher animals. Elastin is most prominent in tissues such as vascular wall, ligament, lungs and skin. In mammals, elastin derives from a single protein, tropelastin, of about 70 kD which on crosslinking of lysine side chains becomes the insoluble elastic matrix that is fibrous elastin. In the pig and cow, the longest sequence between lysine-containing crosslinking sequences is (L-Val$^1$-L-Pro$^2$-Gly$^3$-L-Val$^4$-Gly$^5$)$_{11}$ or (VPGVG)$_{11}$. When high molecular weight poly(VPGVG) is synthesized and cross-linked by $\gamma$-irradiation to form an insoluble matrix, it is found to be elastic with physical properties remarkably similar to fibrous elastin, for example, with an elastic modulus near 10$^6$ dynes/cm$^2$. Yet elastin contains some fifteen glycine-rich hydrophobic sequences between alanine-rich, lysine derived cross-linking regions and the roles of many of the sequences have yet to be determined. Some of these also are seen to contain related repeating sequences. In the pig and cow, the second longest sequence between cross-links is a repeating hexapeptide well-represented by (L-Ala$^1$-L-Pro$^2$-Gly$^3$-L-Val$^4$-Gly$^5$-L-Val$^6$)$_n$ or (APGVGV)$_n$ where n is approximately 5. In man, the hexapeptide repeats eight times in a continuous sequence. High polymers of (APGVGV) are found on raising the temperature in water to form irreversible precipitates and which separate from organic solvents to form matrices. These matrices are not elastic. There is also a less prominent repeat tetrapeptide (L-Val$^1$-L-Pro$^2$-Gly$^3$-Gly$^4$)$_n$ which is elastic. Notably, in all of the above formulae, the standard three-letter or one-letter abbreviations for amino acids are used. See, for example, *Organic Chemistry of Biological Compounds*, pages 56–58 (Prentice-Hall, 1971).

In humans, the longest sequence between cross-links contains a nonapeptide repeat which is well-represented by (L-Val$^1$-L-Pro$^2$-Gly$^3$-$\phi^4$-Gly$^5$-L-Val$^6$-Gly$^7$-L-Ala$^8$-Gly$^9$)$_n$ where $\phi^4$ may be L-Leu$^4$ or L-Phe$^4$ where n is just greater than four. In cows, the polynonapeptide occurs in the third longest sequence where n is four, and in pigs the nonapeptide repeats three times and where $\phi^4$=L-Phe$^4$ in each of the nonamers.

Recently, Urry et al prepared synthetic polypentapeptides and polytetrapeptides, based on the penta- and tetrapeptide repeating units of elastin, and discovered that these peptides could be used to prepare bioelastomeric materials having an excellent modulus of elasticity. This is disclosed and claimed in U.S. Pat. Nos. 4,132,746 and 4,187,852. Moreover, a composite bioelastomeric material based on an elastic polypentapeptide or polytetrapeptide and a strength-giving fiber was disclosed and claimed in U.S. Pat. No. 4,474,851. Additionally, a bioelastomeric material having an increased modulus of elasticity formed by replacing the third amino acid in a polypentapeptide with an amino acid of opposite chirality was disclosed and claimed in U.S. Pat. No. 4,500,700 to Urry and to an enzymatically cross-linked polypeptide as disclosed in and claimed in U.S. Pat. No. 4,589,882. Furthermore, U.S. Pat. No. 4,605,413 is directed to a chemotactic peptide, while U.S. Pat. No. 4,693,718 is directed to a second chemotactic peptide. Also pending is Ser. No. 07/180,677, directed to a segmented polypeptide bioelastomer for the modulation of elastic modulus.

Also issued is U.S. Pat. No. 4,783,523 which describes the temperature correlated force and structure development of various elastomeric polytetrapeptides and polypentapeptides. In that application, Urry et al disclosed that the above polypeptides exhibit elastomeric force development which can be varied as a function of temperature. In particular, it was found that by varying the primary structure of the repeating tetrameric or pentameric unit of the polypeptide that it is possible to effect the range of temperature over which the elastomer develops elastomeric force.

In related work, Urry et al discovered that polypeptides containing the hexapeptide sequence (APGVGV)$_n$ and permutations thereof are chemotactic toward fibroblasts. However, as cross-linked poly-(APGVGV) is not elastic, it has not been possible to produce an elastomeric polypeptide which is chemotactic toward fibroblasts, and which has an elastic modulus as great as 10$^7$ to 10$^8$ dynes/cm$^2$.

Thus, a need clearly continues to exist for elastomeric polypeptides having good elastomeric properties and which also exhibit chemotaxis. Such polypeptides would be expected to be particularly useful in the construction of artificial ligaments or as a scaffolding for the reconstruction of ligament, vascular wall and skin.

SUMMARY OF THE INVENTION

Accordingly, it is an object of the present invention to provide polypeptides having increased elastic moduli.

It is also an object of this invention to provide polypeptides which are also chemotactic toward endothelial cells and fibroblasts.

In particular, it is an object of the present invention to provide elastomeric polynonapeptides which have increased elastic moduli and which are chemotactic toward endothelial cells and fibroblasts.

The above and other objects are provided by a polynonapeptide having the formula:

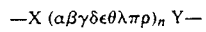

wherein:

$\alpha$ is a peptide-forming residue of L-Valine or another peptide-forming residue capable of functioning in position i of a $\beta$-turn in a polypeptide;

β is a peptide-forming residue of L-Proline or another peptide-forming residue capable of functioning in position i+1 of a β-turn in a polypeptide;

γ is a peptide-forming residue of Glycine or another peptide-forming residue capable of functioning in position i+2 of a β-turn in a polypeptide;

δ is a peptide-forming residue of L-Phenylalanine or another peptide-forming residue capable of functioning in position i+3 of a β-turn in a polypeptide;

ε is a peptide-forming residue of Glycine or D-Alanine, when functioning as position i' of a subsequent β-turn in a polypeptide when δ is as defined above; or ε is as defined above for α,
when δ is Glycine or D-Ala;

θ is a peptide-forming residue of L-Valine or another peptide-forming residue as defined above for α, or when functioning as position (i+1)' of a subsequent β-turn in a polypeptide, θ is a peptide-forming residue as defined above for β;

λ is a peptide-forming residue of Glycine, D-Alanine or another peptide-forming residue as defined above for γ, when functioning as position (i+2)' of a subsequent β-turn in a polypeptide;

π is a peptide-forming residue of L-Alanine or another peptide-forming residue as defined above for δ, when functioning as position (i+3)' in a subsequent β-turn in a polypeptide; or a direct bond;

ρ is a peptide-forming residue of L-Glycine or D-Alanine;

and wherein X is $\beta\gamma\delta\epsilon\theta\lambda\pi\rho$, $\gamma\delta\epsilon\theta\lambda\pi\rho$, $\delta\epsilon\theta\lambda\pi\rho$, $\epsilon\theta\lambda\pi\rho$, $\theta\lambda\pi\rho$, $\lambda\pi\rho$, $\pi\rho$, $\rho$ or a bond; Y is $\alpha\beta\gamma\delta\epsilon\theta\lambda\pi$, $\alpha\beta\gamma\delta\epsilon\theta\lambda$, $\alpha\beta\gamma\delta\epsilon\theta$, $\alpha\beta\gamma\delta\epsilon$, $\alpha\beta\gamma\delta$, $\alpha\beta\gamma$, $\alpha\beta$, $\alpha$ or a direct bond; and n has a value of 1 to about 5,000; and with the proviso that no more than three of residues ε, θ, λ, π and ρ are simultaneously a peptide-forming residue of Glycine.

The present invention will now be further explained by reference to the following drawings which are provided only for the purpose of illustration.

DETAILED DESCRIPTION OF THE PREFERRED EMBODIMENT

Figure 1:
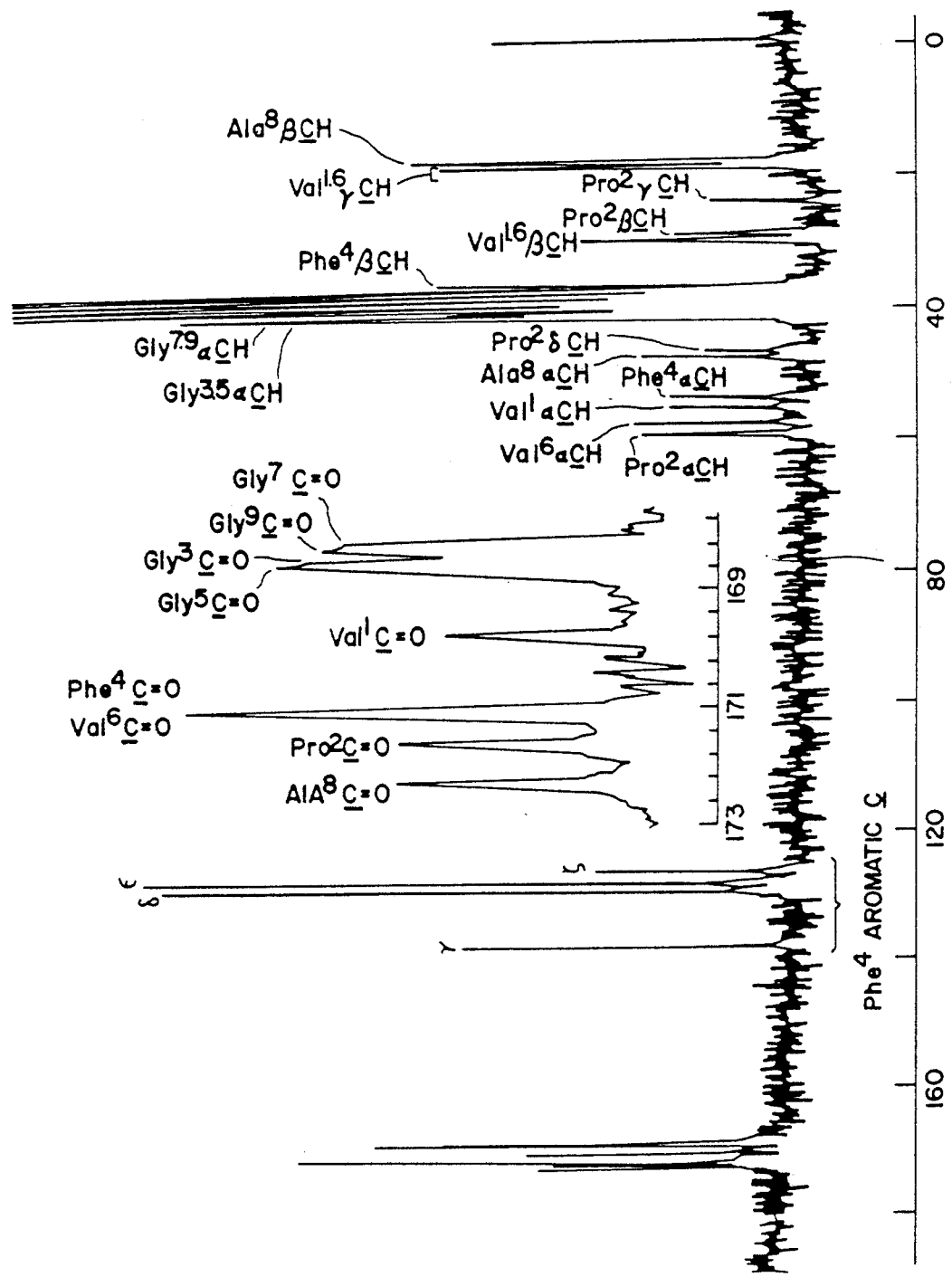
FIG. 1 represents a 25.15 MHz $^{13}$C-NMR spectrum of poly(VPGFGVGAG). 30 mg. of sample was dissolved in 0.5 ml of DMSO-$d_6$ and the spectrum was obtained after 77,000 scans with a spectral width of 5 KHz, pulse repetition time of 1 sec and 8K data points. Peak assigment is based on the unpublished results of two dimensional $^{13}$C-$^1$H chemical shift correlation spectroscopy experiments.

A typical biological elastic fiber is comprised of a large elastin core covered with a fine surface layer of microfibrillar protein. Elastin is formed upon cross-linking of the lysine residues of tropoelastin. The repeating elastin pentapeptide has the formula (VPGVG)$_n$, while the repeating hexapeptide has the formula (VAPGVG)$_n$, where n varies depending upon the species. The repeating polytetrapeptide unit has the formula (VPGG)$_n$. These sequences, as noted above, utilize the standard one-letter abbreviation for the constituent amino acids.

It was found that these polypeptides are soluble in water below 25° C., but on raising the temperature they associate in the polypentapeptide (PPP) and polytetrapeptide (PTP) cases, reversibly to form a viscoelastic phase, and in the polyhexapeptide (PHP) case, irreversibly to form a precipitate. On cross-linking, the former (PPP) and (PTP) have been found to be elastomers. However, cross-linked PHP is not elastic.

At temperatures above 25° C. in water, PTP and PPP exhibit aggregation and form a water-containing viscoelastic phase, which upon cross-linking by γ-irradiation forms an elastomer. By contrast, PHP forms a granular precipitate, which is not elastomeric. In fact, for potential elastomers, such aggregation is readily reversible, whereas for non-elastomeric samples, such as PHP, temperature-driven aggregation is irreversible and redissolution usually requires the addition of a solvent such as trifluoroethanol to the aggregate.

Cross-linked PPP, PTP and analogs thereof were found to exhibit elastomeric force development at different temperatures spanning a range of up to about 75° C. depending upon several controllable variables. Moreover, for these cross-linked elastomers the development of near maximum elastomeric force occurs over a very narrow temperature range. Thus, by synthesizing bioelastomeric materials having varying molar amounts of the constituent pentamers and tetramers together with such units modified by hexameric repeating units, and by choosing a particular solvent to support the initial viscoelastic phase which forms, it became possible to rigorously control the temperature at which the obtained bioelastomer develops elastomeric force. Further modification may now be effected using the polynonapeptides disclosed herein.

For example, by modifying PPP, the temperature of transition may be changed. In particular, by increasing the hydrophobicity of the PPP repeating unit, the viscoelastic phase transition occurs at lower temperatures, while by decreasing the hydrophobicity of the repeating unit, this transition occurs at higher temperatures. Importantly, it was found possible to modify the hydrophobicity in such a way that elasticity is retained.

For example, modifications of the repeating pentamers have been made which destroy the molecular structure required for elasticity, such as the Ala$^1$ and Ala$^5$ analogs. The Ala$^1$ and Ala$^5$ analogs, the former decreasing and the latter increasing pentamer hydrophobicity, result in the formation of granular precipitates on raising the temperature of aqueous solutions rather than forming viscoelastic coacervates and γ-irradiation cross-linking of the Ala$^5$-PPP precipitate results in a hard material that simply breaks upon stretching. These analogs apparently fail to produce elastomeric polymers for different but consistent reasons First, the Ala¹ analog does not appear to allow for important Val¹ ... γCH₃ ... Pro² δCH₂ intrapentameric intramolecular hydrophobic contacts required to form a viscoelastic coacervate. The Ala⁵ analog appears to interfere with librational motions in the Val⁴-Gly⁵-Val¹ suspended segment of the proposed PPP molecular structure. Similarly, the Ala⁹ polynonapeptide analog would be expected to interfere with librational motions in the Val⁸-Gly⁹-Val¹ or Ala⁸-Gly⁹-Val¹ suspended segments. These librational motions appear to be essential to the proposed librational entropy mechanism of elasticity for these elastomers.

By contrast, the hydrophobicity of the repeating pentamer has been easily increased by introducing a —CH₂— moiety, for example, in residue 1 while maintaining β-branching, that is, to utilize the Ile analog of PPP, i.e., (Ile¹-Pro²-Gly³-Val⁴-Gly⁵)$_n$. With a greater than 50,000 molecular weight, Ile¹-PPP reversibly forms a viscoelastic coacervate with the onset of coacervation being near 8° C. rather than 24° C. as for unsubstituted PPP. It appears from circular dichroism data that Ile¹-PPP and PPP have identical conformations both before and after the transitions and that the transition to increased intramolecular order on increasing the temperature is also shifted by 15° C. or more to lower temperatures. Further, the dramatic increase in elastomeric force on raising the temperature of the γ-irradiation cross-linked coacervate at fixed extension is similarly shifted to a lower temperature for the Ile¹-PPP analog. Thus, with this analog, a coupling of temperature dependent elastomeric force development and molecular structure was demonstrated. Hence, it is now possible to rationally design polypeptide elastomers that undergo transitions at different temperatures and that would function as entropic elastomers in different temperature ranges.

By increasing the hydrophobicity of PPP, such as by substituting Ile¹ for Val¹ in the pentameric sequence of —(VPGVG)$_n$ to form —(IPGVG)$_n$—, it became possible to accomplish at least two distinct objectives.

First, the "homopolymeric" polypentapeptide of —(IPGVG)$_n$, can be prepared i.e., Ile¹-PPP, which, as noted dissolves in water at 4° C., and upon raising the temperature to 8° C., exhibits aggregation. After cross-linking the coacervate by γ-irradiation, it is observed that essentially full elastic contraction is exhibited at about 25° C. for the cross-linked Ile¹-PPP as opposed to the 40° C. temperature required for the unsubstituted PPP. Thus, the temperature ordered transition for Ile¹-PPP occurs at a temperature approximately 15° C. lower than for PPP.

Secondly, mixed "copolymers", for example, of the polypentapeptides —X¹—(IPGVG)$_n$—Y¹— and —X²—(VPGVG—)$_n$—Y²— can be prepared which exhibit variable and controllable transition temperatures which are in between the separate transition temperatures of PPP and Ile¹-PPP. Further, a great degree of control became possible inasmuch as the transition temperature obtained is directly proportional to the molar ratios of the respective pentapeptides incorporated therein.

As noted above, it was recently discovered that hexapeptide segments of the formula VGVAPG and permutations thereof are chemotactic toward fibroblasts and endothelial cells. However, because cross-linked PHP is not elastic, it has not been possible to prepare polypeptides which are, at once, both elastomeric and chemotactic toward fibroblasts and endothelial cells and which have a modulus of elasticity of about 10⁷ to 10⁸ dynes/cm².

The present invention, therefore, provides, for the first time, polypeptides which have both increased elastomeric properties and which are chemotactic toward fibroblasts and endothelial cells.

In general, the present invention provides a polynonapeptide of the formula:

—X (αβγδεθλπρ)$_n$ Y— wherein:

α is a peptide-forming residue of L-Valine or another peptide-forming residue capable of functioning in position i of a β-turn in a polypeptide;

β is a peptide-forming residue of L-Proline or another peptide-forming residue capable of functioning in position i+1 of a β-turn in a polypeptide;

γ is a peptide-forming residue of L-Glycine or another peptide-forming residue capable of functioning in position i+2 of a β-turn in a polypeptide;

δ is a peptide-forming residue of L-Phenylalanine or another peptide-forming residue capable of functioning in position i+3 of a β-turn in a polypeptide;

ε is a peptide-forming residue of Glycine or D-Alanine, when functioning as position i' of a subsequent β-turn in a polypeptide when δ is as defined above, or ε is as defined above for α when δ is glycine or D-Alanine;

θ is a peptide-forming residue of L-Valine or another peptide-forming residue as defined above for α or a direct bond;

λ is a peptide-forming residue of Glycine, D-Alanine or another peptide-forming residue as defined above for α; or when functioning as position (i+1)' of a subsequent β-turn in a polypeptide, θ is a peptide-forming residue as defined above for β;

π is a peptide-forming residue of L-Alanine or another peptide-forming residue as defined above for δ when functioning as position (i+2)' in a subsequent β-turn in a polypeptide or a direct bond;

ρ is a peptide-forming residue of L-Glycine, D-Alanine;

wherein X is βγεδθλπρ, γδεθλπρ, δεθλπρ, εθλπρ, θλπρ, λπρ, πρ, ρ or a direct bond; Y is αβγδεθλπ, αβγδεθλ, αβγδεθ, αβγδε, αβγδ, αβγ, αβ, α or a direct bond; and n has a value of 1 to about 5,000; and with the proviso that no more than three of residues ε, θ, λ, π and ρ are simultaneously a peptide-forming residue of Glycine.

The polynonapeptides of the present invention can be produced as "homopolymer" nonapeptides or one or more of the present nonapeptide sequences may be chemically bonded to other elastomeric sequences such as the PPP or PTP sequences described above or those sequences with the appropriate substitutions as may be required to modify the temperature of transition. Additionally, polyhexapeptide sequence, PHP and modifications as will be described, can also be included.

For purposes of comprehending the present invention, the preparation and use of various PPP or PTP sequences, with and without substitution, will first be briefly discussed. Thereafter, the preparation and use of the polynonapeptides will be described.

PPP cross-linked analogs having increased hydrophobicity were found to develop full elastomeric force over a very narrow temperature range. For example, for crosslinked Ile¹-PPP, it was found that the elastomeric force thereof shows an abrupt increase from essentially zero at 8° C. to three-quarters of full force at 10° C., and essentially full force by 20°-25° C. Such an increase in elastomeric force over only a 2° C. temperature differential is, indeed, unprecedented and can be controlled by the percent extension in relation to swelling of the elastomer on lowering the temperature.

Although Ile[1]-PPP is an excellent example of an increased hydrophobicity PPP analog, any PPP analog, which increases the hydrophobicity of the repeating pentameric unit, while retaining the elasticity of the polypeptide, and without interfering with either the formation of the viscoelastic coacervate or the librational motion may be used.

For example, in addition to repeating unit sequences of $(IPGVG)_n$, using Ile[1], is also possible to effect a variety of other substitutions. In general, a pentapeptide repeating unit of the formula:

$$-(R_1PR_2R_3G)_n-$$

can be used, wherein $R_1$ may be Phe, Leu, Ile, Val, Tyr and Trp; $R_2$ may be Ala and Gly; $R_3$ may be Phe, Leu, Ile, Met, Ala and Val; and n is an integer from 1 to 5,000, and P is L-proline and G is glycine.

Notably, the above substitutions modify the hydrophobicity of the repeating unit so as to attenuate the transition temperature for near maximum elastomeric force development, of course, without destroying the elasticity of the bioelastomer.

In the above formula, it is noted that the amino acid Leu is, of course, Leucine. $R_1$, $R_2$ and $R_3$ correspond to positions 1, 3 and 4 in the numbered sequence as described herein.

Interestingly, with about 50% Phe[1]-PPP in water, it is possible to shift the temperature of transition initiation from 25° C. for PPP to about 0° C. Furthermore, this shift can be driven to even lower temperatures by utilizing mixed solvent systems of water/ethylene glycol or water/dimethyl sulfoxide (DMSO). For example, by using the about 50% Phe[1]-PPP/water-ethylene glycol system, a transition temperature of as low as about −25° C. can be obtained. Of course, a range of transition temperatures can be obtained between 0° C. and about −25° C. for the Phe[1]-PPP/water-ethylene glycol system depending upon the amount of ethylene glycol added. It has been found that very low transition temperatures are obtained using approximately 50/50 mixtures of water/ethylene glycol.

Conversely, the maximum shift to higher transition temperatures is limited by further structural change to the polypeptide. With the present elastomeric polypeptides, this upper limit appears to be about 50° C. with transition to a less elastic state beginning at about 60° C.

However, as noted previously, not only are PPP analogs contemplated, such as Ile[1]-PPP, Phe[1]-PPP or Ala[3]-PPP, but all PPP analogs, and bioelastomers containing the same, which have transition temperatures, and; hence, temperatures of near maximum elastomeric force development, which are different from PPP; while retaining elasticity are contemplated. Given, the present disclosure, one skilled in the art could clearly ascertain additional PPP analogs, and bioelastomers incorporating the same which meet the above criteria.

As noted above, the increased hydrophobicity analog, such as Ile[1]-PPP may be synthesized as a "homopolymer", or a "copolymer" of $-X^2-(VPGVG-)_n-Y^2-$ and $-X^1-(IPGVG-)_n-Y^1-$ may be synthesized with the molar ratio of the constituent pentamers being dependent upon the desired temperature for elastomeric force development. However, in general, in such "copolymers", the $-X^1-(IPGVG-)_n-Y^1-$ pentameric component is present in about 1-99% of the total pentameric molar content, while the $-X^2-(VPGVG-)_n-Y^2-$ pentameric component is present in about 99-1% of the total pentameric content. More preferably, the $-X^1-(IPGVG)_n-Y^1-$ component is present in about 5-95% of the total pentameric molar content, while the $-X^2-(VPGVG-)_n-Y^2-$ component is present in about 95-5% of the total pentameric molar content. However, any combination of relative molar amounts can be used as dictated by the desired transition temperature.

Thus, bioelastomers can be prepared which contain repeating units containing elastomeric tetrapeptide, or pentapeptide or units thereof modified by hexapeptide repeating units and mixtures thereof, wherein said repeating units contain amino acid residues selected from the group consisting of hydrophobic amino acid and glycine residues, wherein the repeating units exist in a conformation having a β-turn which contains a polypentapeptide unit of the formula:

$$-X^1-(IPGVG-)_n-Y^1-$$

wherein I is a peptide-forming residue of L-isoleucine;
  P is a peptide-forming residue of L-proline;
  G is a peptide-forming residue of glycine;
  V is a peptide-forming residue of L-valine; and
wherein X is PGVG, GVG, VG, G or a covalent bond; Y is IPGV, IPG, IP or I or a covalent bond; and n in both formulas is an integer from 1 to 5,000; or n is 0, with the proviso that $X^1$ and $Y^1$ together constitute a repeating pentapeptide unit, in an amount sufficient to adjust the development of elastomeric force of the bioelastomer to a predetermined temperature.

However, bioelastomers can also be prepared which contain elastomeric units comprising tetrapeptide, or pentapeptide or units thereof modified by hexapeptide repeating units and mixtures thereof, wherein said repeating units comprise amino acid residues selected from the group consisting of hydrophobic amino acid and glycine residues, wherein the repeating units exist in a conformation having a β-turn which comprises (A) a polypentapeptide unit of the formula:

$$-X^1-(IPGVG-)_n-Y^1-$$

and (B) a polypentapeptide unit of the formula:

$$-X^2-(VPGVG-)_n-Y^2-$$

wherein for the above formulas,
  I is a peptide-forming residue of Lisoleucine;
  P is a peptide-forming residue of L-proline;
  G is a peptide-forming residue of glycine;
  V is a peptide-forming residue of L-valine; and
wherein $X^1$ and $X^2$ are each PGVG, GVG, VG, G or a covalent bond; $Y^1$ is IPGV, IPG, IP or I or a covalent bond; $Y^2$ is VPGV, VPG, VP, V or a covalent bond; and n in both formulas an integer from 1 to 5,000; or n in both formulas is 0, with the proviso that $X^1$ and $Y^1$ together, and $X^2$ and $Y^2$ together constitute a repeating pentapeptide unit, in relative amounts sufficient to adjust the development of elastomeric force of the bioelastomer to a predetermined temperature.

It should be noted that bioelastomeric polypeptide chains containing either one or both of the above pentapeptide repeating units can be synthesized using any of the pentapeptide "monomers" that are permutations of the basic sequence. However, if the polymer is not synthesized using the pentapeptide "monomers", but rather is synthesized by sequential adding of amino acids to a growing peptide, such as in the case of an automatic peptide synthesizer, the designation of the repeating unit is somewhat arbitrary. For example, the peptide H—V(PGVGVPGVGVPGVGVPGVGV-)P—OH can be considered to consist of any of the following repeating units and end groups: H—(VPGVG-)$_4$—VP—OH, H—V—(PGVGV)$_4$—P—OH, HVP(GVGVP) $_4$—OH, H—VPG—(VGVPG)$_3$—VG-VP—OH, or H—VPGV—(GVPGV)$_3$—GVP—OH, for example.

Furthermore, it is entirely possible that mixed repeating units such as those of the formula —VPG-VGIPGVG—$_n$ can be incorporated into the bioelastomers.

Synthesis of the elasticity promoting and modifying segments, which are incorporated into the final elastomeric polypeptide, is straightforward and easily accomplished by a peptide chemist. The resulting intermediate peptides generally have the structure, $B^1$-(repeating unit)$_n$-$B^2$ where $B^1$ and $B^2$ represent any chemically compatible end group on the amino and carboxyl ends of the molecule, respectively, and n is an integer of from 1 to about 5,000. Of course, when $B^1$ is —H and $B^2$ is —OH, and n is 1, the compound is either the pentapeptide H—VPGVG—OH or HIPGVG—OH. When n is greater than 1, the compound intermediate is a polypentapeptide. The same will hold true when utilizing tetrameric repeating units in the present bioelastomers.

It should be noted that the term "hydrophobic amino acid" refers to amino acids which have appreciably hydrophobic R groups as measured on a hydrophobicity scale generated by measuring the relative solubilities of the amino acids in organic solvent. In this respect, see *Arch. Biochem. Biophy*, Bull and Breese Vol. 161, 665–670 (1974). By this method, all amino acids which are more hydrophobic than glycine may be used. More specifically, preferable hydrophobic amino acids are Ala, Val, Leu, Ile, Pro, Met, Phe, Tyr and Trp.

Further, in order to allow the present elastomers to be switched "on" and "off" at fixed length, it is not necessary to restrict the amino acids utilized to only those having hydrophobic R groups. While one or more amino acids having polar R groups are preferable for using the switching mechanism, it is only necessary to maintain an appropriate mean or average hydrophobicity. Of particular interest, however, are amino acids having ionizable R groups, such as Glu, Asp, His, Lys or Tyr or even hydroxyl-containing or sulfhydryl-containing R groups which can be phosphorylated or otherwise chemically modified, such as Ser, Thr, Tyr, Hyp and Cys.

Additionally, it is permissible that one or more amino acid residues or segments of amino acid residues not present in the normal pentapeptide or tetrapeptide sequence may be interspersed within a polypentapeptide or polytetrapeptide portion of an elastomeric polypeptide chain.

Thus, these bioelastomers, regardless of the particular functional repeating unit incorporated therein, may have these repeating units incorporated either in the form of block or random copolymers as long as the desired shift in temperature of elastomeric force development of the bioelastomer is obtained. As noted above, by considering the transition temperatures and temperatures of elastomeric force development for two PPP or PTP analogs, or even for a PPP analog and a PTP analog, it is possible to attain a desired intermediate transition temperature and temperature of elastomeric force development by directly correlating the molar ratios of each analog component therewith. For example, a 50/50 molar ratio of two analog components would give rise to a bioelastomer "copolymer" having a transition temperature and temperature of elastomeric force development approximately in between those of the analog components.

Additionally, it is also noted that the elastomeric units used in conjunction with all aspects of the present invention, i.e., whether the repeating unit is PPP, PTP or analogs thereof, may also comprise those described in U.S. Pat. Nos. 4,132,746, 4,187,852; 4,474,851; 4,500,700, 4,589,882, 4,605,413, 4,693,718 and 4,783,523 and U.S. Pat. application Ser. Nos. 07/180,677, 07/062,557, 07/163,388 and 07/184,147 all of which patents and patent applications are incorporated herein in their entirety.

The preparation of PPP and analogs thereof will now be illustrated by Examples, which are provided only for the purpose of illustration and are not intended to be limiting.

EXAMPLES

Peptide Synthesis

The synthesis of Ile$^1$-PPP was carried out by the classical solution methods as shown in Scheme I.

In the following Examples, the following abbreviations will be used: Boc, tert-butyloxycarbonyl; Bzl, benzyl; DMF, dimethylformamide; DMSO, dimethylsulfoxide; EDCI, 1-(3-dimethylaminopropyl)-3ethylcarbodiimide; HOBt, 1-hydroxybenzotriazole; IBCF, isobutyl-chloroformate; NMM, N-methylmorpholine; ONp, p-nitrophenylester; TFA, trifluoroacetic acid; PPP, (VPGVG)$_n$; Ile$^1$-PPP, (IPGVG)$_n$; V, valine; I, isoleucine; P, proline; G, glycine.

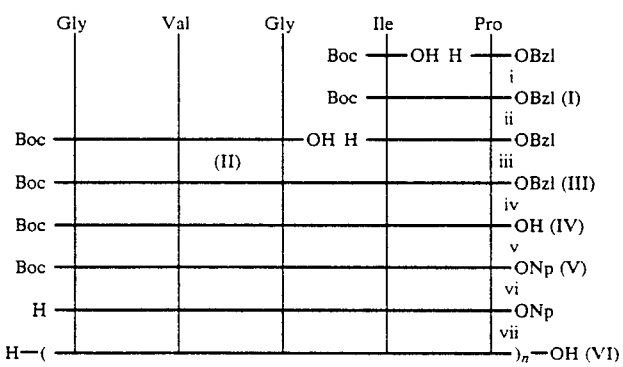

Scheme I
Synthesis of H—(Gly—Val—Gly—Ile—Pro)$_n$—OH (i) IBCF/HOBt;
(ii) HCL/Dioxane;
(iii) EDCI/HOBt;
(iv) H$_2$—Pd/C;
(v) Bis (p-nitrophenyl)carbonate;
(vi) TFA;
(vii) DMSO—NMM The sequence of the starting pentamer for polymerization is preferably Gly-Val-Gly-Ile-Pro rather than Ile-Pro-Gly-Val-Gly, because the permutation with Pro as the C-terminal amino acid produces high molecular weight polymers in better yields. The approach to the synthesis entailed coupling the tripeptide Boc-GVG-OH (II) with H-IP-OBzl, each in turn being synthesized by the mixed anhydride methodology of J. R. Vaughan et al, *J. Am. Chem. Soc.*, 89, 5012 (1967). The possible formation of the urethane as a by-product during the reaction of Boc-Ile-OH with H-Pro-OBzl by the mixed anhydride method was avoided by carrying out the reaction in the presence of HOBt. The dipeptide was also prepared using EDCI for confirmation of the product. The pentapeptide benzylester (III) was hydrogenated to the free acid (IV) which was further converted to the p-nitrophenylester (V) on reacting with bis(p-nitrophenyl)carbonate. On removing the Boc-group, a one molar solution of the active ester in DMSO was polymerized in the presence of 1.6 equiv. of NMM. The polypeptide was dialyzed against water using a 50,000 dalton cut-off dialysis tubing and lyophilized. The purity of the intermediate and final products was checked by carbon-13 nuclear magnetic resonance, elemental analyses and thin layer chromatography (TLC).

Elemental analyses were carried out by Mic Anal, Tuscon, AZ. All amino acids are of L-configuration except for glycine. Boc-amino acids were purchased from Bachem, Inc., Torrance, CA. HOBt was obtained from Aldrich Chemical Co., Milwaukee, WI. TLC was performed on silica gel plates purchased from Whatman, Inc., Clifton, NJ in the following solvent systems: R$_f^1$, CHCl$_3$ (C):CH$_3$OH(M):CH$_3$COOH(A), 95:5:3; R$_f^2$, CMA (85:15:3); R$_f^3$, CMA (75:25:3); R$_f^4$, CM (5:1). Melting points were determined with a Thomas Hoover melting point apparatus and are uncorrected.

Boc-Ile-Pro-OBzl (mixed anhydride method) (I): Boc-Ile-OH (12.01 g, 0.05 mole) in DMF (50 ml) was cooled to 0° C. and NMM (5.49 ml) was added. After cooling the solution to −15° C. isobutylchloroformate (6.48 ml) was added slowly while maintaining the temperature at −15° C. and stirred for 10 minutes at which time HOBt (7.65 g) was added and stirring was continued for additional 10 minutes. A pre-cooled solution of HCl-H-Pro-OBzl (12.09 g, 0.05 mole) in DMF (50 ml) and NMM (5.49 ml) was added to the above solution and the completeness of the reaction was followed by TLC. The reaction mixture was poured into a cold saturated NaHCO3 solution and stirred for one hour. The peptide was extracted into CHCl$_3$ and washed with acid and base (0.5 N NaOH to remove HOBt), and on evaporating the solvent the product was obtained as an 92% yield. R$_f^1$, 0.65. Anal. Calcd. for C$_{23}$H$_{34}$N$_2$O$_5$: C 66.00, H 9.19, N 6.69%. Found: C 65.58, H 8.28, N 7.13%.

Boc-Ile-Pro-OBzl (using EDCI): Boc-Ile-OH (7.20 g, 0.03 mole) and HOBt (5.05 g, 0.033 mole) in DMF (30 ml) was cooled to −15° C. and EDCI (6.32 g, 0.033 mole) was added. After stirring for 20 minutes, a pre-cooled solution of HCL-HPro-OBzl (7.25 g, 0.103 mole) in DMF (30 ml) and NMM (3.3 ml) was added and stirred overnight at room temperature. After evaporating DMF, the residue was taken into CHCl3 and extracted with 20% citric acid and 0.5 N NaOH. The solvent was removed and the product was obtained as an oil in almost quantitative yield which was identical to the product obtained by the mixed anhydride method.

Boc-Gly-Val-Gly-Ile-Pro-OBzl (III): Boc-GVG-OH (II) (20) (5.6 g, 0.017 mole) was coupled with H-Ile-Pro-OBzl (6.7 g, 0.019 mole) (obtained by deblocking I with HCl/Dioxane) in the presence of EDCI (3.65 g, 0.019 mole) and HOBt (2.9 g, 0.019 mole) and the product was worked up as described above to obtain 8.8 g of III (yield: 82.4%), m.p. 107°–108° C. (decomp.) R$_f^2$, 0.75 Anal. calcd. C$_{32}$H$_{49}$N$_5$O$_{10}$: C 60.83, H 7.81, N 11.08%. Found: C 61.12, H 8.06, N 11.06%.

Boc-Gly-Val-Gly-Ile-Pro-OH (IV): III (7.8 g, 0.0123 mole) was taken in acetic acid (80 ml) and hydrogenated in the presence of 10% Pd-C (1 g) at 40 psi. After filtering the catalyst with the aid of celite, the solvent was removed under reduced pressure, triturated with ether, filtered, washed with ether then pet. ether and dried to obtain 6.5 g of the product (yield: 97.3%), m.p. shrinks at 127° C. and decomp. at 3 145° C. R$_f^3$, 0.24; R$_f^4$, 0.11 Anal. Calcd. for C$_{25}$H$_{43}$N$_5$O$_{10}$.1/2H$_2$O: C 54.52, H 8.05, N 12.71%. Found: C 54.32, H 8.02, N 12.59%.

Boc-Gly-Val-Gly-Ile-Pro-ONp (V): IV (5.41 g, 0.01 mole) in pyridine (40 ml) was reacted with bis(p-nitrophenyl)carbonate (4.56 g, 0.015 mole) following the completeness of the reaction by TLC. Pyridine was removed; the residue was taken into $CHCl_3$ and extracted with acid and base. The p-nitrophenyl ester obtained was chromatographed over a silica gel (200–400 mesh) column. After initial washing with $CHCl_3$ 4.8 g of V was obtained when eluted with 35% acetone in $CHCl_3$ (yield: 71.4%), m.p. 97°–100° C. $R_f^2$, 0.72; $R_f^4$, 0.75; Anal. Calcd. for $C_{31}H_{45}N_6O_{12}\cdot 2H_2O$: C 53.28, H 7.21, N 12.02%. Found: C 53.76, H 6.83, N 12.01%.

H-(Gly-Val-Gly-Ile-Pro)$_n$-OH(VI): The Boc-group was removed from V (3.8 g, 0.0057 mole) by reacting with TFA (35 ml) for 45 min. TFA was removed under reduced pressure, triturated with ether, filtered, washed with ether, pet. ether and dried. The TFA salt (3.3 g, 0.0049 mole) in DMSO (4.9 ml) was stirred for 14 days in the presence of NMM (0.86 ml, 0.0078 mole). After diluting with water in the cold, the polypeptide was dialyzed using a 50 kD cut-off dialysis tubing changing the water daily for 15 days. The retentate was lyophilized to obtain 1.81 g of the $Ile^1$-polypentapeptide (yield: 88%). The carbon-13 NMR spectrum is presented in FIG. 1 along with that of the regular polypentapeptide for comparison.

In addition to the above synthetic methods for synthesizing the PPP polypeptide elastomers of the present invention, the elastomers of the present invention may also be prepared by microbial biosynthesis. In particular, microbial biosynthesis may be effected by using well-known techniques of genetic engineering using suitable host organisms such as *E. coli* and plasmid vectors capable of expression therein. Of course, by using the gene splicing technique, a gene sequence corresponding to the desired elastomeric polypeptide sequence is inserted into a suitable plasmid vector using known techniques, which hybrid plasmid is then inserted into a suitable host organism, such as *E. coli*. The resultant transformed microorganism is then cultured in accordance with known fermentative techniques to afford the product bioelastomer.

Notably, recombinant microbial synthesis can also be used to synthesize PTP, PTP/PPP and PTP/PPP/PHP combinations and any or all of these combinations with a polynonapeptide (PNP). Of course, it can also be used to synthesize all of the various polar-substituted polypeptide elastomers involved in chemomechanical transduction.

As noted above, *E. coli* expression systems for amino acid and peptide synthesis are well known. U.S. Pat. Nos. 4,278,765, 4,321,325 and 4,264,731 are hereby incorporated herein in the entirety.

Temperature Profiles for Coacervation

The temperature dependence for aggregation of the polypentapeptide is followed as the development of turbidity at 300 nm using a Cary 14 spectrophotometer. The sample cell is placed within a chamber vibrating at 300 Hz in order to facilitate equilibrium and to keep the aggregates from settling. The scan rate is 30° C./hour and the temperature was controlled with a Neslab ETP-3 programmer and monitored with an Omega 199A thermocouple monitor placed at the cell. The turbidity as a function of temperature provides a temperature profile for coacervation which is found to be concentration dependent. As the concentration is raised, the profile shifts to lower temperatures until further increases in concentration cause no further lowering of the temperature for aggregation. This defines the high concentration limit. The temperature for the onset of coacervation at the high concentration limit coincides with the temperature for the onset of the transition within the coacervate itself, even when there is no appreciable change in water content of the coacervate. The temperature for the midpoint of the temperature profile for the high concentration limit has been shown to correlate with the molecular weight of the polypentapeptide. When the midpoint is 25° C. for the PPP, the molecular weight is close to 100,000 daltons as calibrated by dialysis. For the $Ile^1$-PPP with a midpoint of 9° C., the molecular weight is greater than 50,000 daltons, as the synthetic polypeptide was retained by a 50,000 daltons dialysis membrane. The dialysis was carried out at 4° C. where the Ile1-PPP is in solution.

Circular Dichroism Measurements

The circular dichroism studies were carried out on a Cary 60 spectropolarimeter equipped with a Model 6001 CD accessory modified for 330 Hz modulation of the left and right circularly polarized light. A concentration of 0.025 mg $Ile^1$-PPP/ml of doubly distilled water was characterized in a 10 mm path length cell. The low concentration was used to keep the size of the aggregate sufficiently small as not to cause light scattering distortions of the CD spectra. Even at this low concentration with this more hydrophobic polypentapeptide, above 35° C. the size of the aggregates was sufficient to cause particulate distortions as was apparent with the red shifting and dampening of the long wavelength negative band. The temperature was controlled and monitored from the cell as for the temperature profiles for coacervation.

Formation of the Elastomeric Matrix

In preparation for γ-irradiation cross-linking (the means of forming the elastomeric matrix), 130 milligrams of peptide $Ile^1$-PPP were dissolved in 220 milligrams of water in a cryotube. The sample was then shear oriented at 0° C. in a previously described pestle-cryotube arrangement. Gamma-irradiation was carried out at the Auburn University Nuclear Science Center at a dose rate of approximately 8,000 Roentgen/min and for sufficient time to achieve a $20 \times 10_6$ radiation absorbed dose (20 Mrad).

Thermoelasticity Studies

Thermoelasticity studies were carried out on a stress-stain instrument built in this Laboratory. The sample is mounted in two Delrin clamps. The top clamp is attached to a Statham UTC strain-gauge and the assembly is fixed. The bottom clamp is attached to a moving platform driven by a variable speed motor. Both clamps are enclosed in a thermostated water jacket. An inner chamber contains the solvent in which the elastomer is immersed which in this case is doubly distilled water. The sample was fixed in the top clamp and equilibrated in water at 60° C. for about an hour. The strain-gauge signal conditioner was balanced for zero force and the bottom clamp was attached to the sample. The sample was left to set overnight at room temperature. The bottom clamp was then adjusted for zero force and the distance between the clamps was measured. The elastomer was elongated to 40% extension at 5° C. and elastomeric force was then determined as a function of temperature. Equilibrium time to achieve constant force at a given temperature was typically twenty-four hours. Force measurements were made in 2° C. increments through the sharp rise in force and 5° C. increments at higher temperatures.

RESULTS

Temperature Profiles for Coacervation

The Ile$^1$-PPP can be dissolved in water on standing below 8° C. On raising the temperature of the solution above 8° C., the solution becomes cloudy; on standing at the elevated temperature settling occurs and a viscoelastic phase forms in the bottom of the vial; on placing the vial in an ice bath the cloudiness immediately clears and the viscoelastic phase readily dissolves. Thus the Ile$^1$-PPP coacervates when dissolved in water. The temperature profiles for As the concentration is raised, the temperature profile shifts to lower temperature. At 40 mg/ml, the high concentration limit (i.e., the lower concentration for which further increases in concentration cause no further lowering of the temperature for the onset of aggregation), the midpoint for the temperature profile for coacervation of Ile$^1$-PPP is 9° C.

It was observed that the simple addition of a CH$_2$ moiety to the 409 dalton repeating unit causes the onset of aggregation to shift to lower temperatures by 16° C.

Circular Dichroism

Determined are the circular dichroism curves for Ile$^1$-PPP in water (0.025 mg/ml) at 2° C. and at 35° C. The low concentration was chosen in order that the size of the aggregate formed on association at 35° C. would have limited particulate distortions in the CD spectrum. At low temperature there is a large negative band near 195 nm. Such a negative band is characteristic of disordered proteins and polypeptides, though a standard value for this negative peak for complete disorder is $-4 \times 10^4$ rather than the observed value of $-1.2 \times 10^4$ Also the negative band near 220 nm, rather than zero ellipticity or a positive band which are taken as indicative of complete disorder, suggests elements of order at low temperature. Furthermore, Raman studies have shown the presence of the $\beta$-turn at temperatures below the transition. Thus, as far as the CD spectra are concerned what is observed is an unmasking of the $\beta$-turn spectrum. The decrease in intensity of the negative CD band near 195 nm on raising the temperature of Ile$^1$-PPP in water indicates an increase in intramolecular order on raising the temperature, that is, there is an inverse temperature transition in an aqueous system. This indicates that hydrophobic interactions are developing as the ordered state develops. The intramolecular increase in order begins just above 0° C. and is complete by about 30° C. for a concentration of 0.025 mg/ml. It was observed that Ile$^1$-PPP and PPP have essentially identical conformations below the onset temperature for the transition and that they have essentially identical conformations after the transition is mostly completed. Thus while maintaining essentially identical conformations, which is assisted by the retention of $\beta$-branching, the addition of a CH$_2$ moiety lowers the transition toward increased order by about 15° C.

Characterization of Elasticity

The elastic (Young's) modulus determined for 20 MRAD cross-linked Ile1-pPP coacervate was $4 \times 10^5$ dynes/cm$^2$ which is within the range of values obtained for 20 Mrad cross-linked PPP. The range of values is due to variable vacuolization occurring during $\gamma$-irradiation which makes difficult accurate measurement of cross-sectional area. It should be appreciated, however, that $\gamma$-irradiation causes no detectable polymer breakdown when measured by carbon-13 and nitrogen-15 NMR.

The results obtained demonstrate with three different physical methods that the addition of a CH$_2$ moiety (the replacement of Val by Ile) shifts the transition to lower temperatures by 15° C. without changing the conformation of the polypentapeptide before and after the transition. While the previously reported data on the naturally occurring PPP of elastin demonstrate a correlation of increased structural order with increased elastomeric force, the Ile$^1$-PPP data with the transition shifted by 15° C. appear to confirm an obligatory coupling of increased order with increased elastomeric force at fixed extension.

The above described hydrophobic effect upon transition temperatures was also observed for the elastin polytetrapeptide, (Val$^1$-Pro$^2$-Gly$^3$-Gly$^4$)$_n$. That is, it was also shown that high molecular weight PTP undergoes a reversible temperature elicited aggregation with an onset of aggregation at 48° C., rather than 24° C. as for high molecular weight PPP.

However, it also been found that the inverse temperature transition for PTP is only complete at about 70° C. This high temperature of transition is due to the lower hydrophobicity of PTP, and of poly VPGAG, as compared to PPP.

For example, utilizing the Bull-Breese hydrophobicity scales with the hydrophobicity of the Gly residue taken as zero, the free energy of transfer for the pentamer, VPGVG, would be $-4100$ cal/mole whereas that of the tetramer, VPGG, would be $-2540$ cal/mole. Thus, if hydrophobicity of the repeating unit is the determining factor, then the inverse temperature transition for the PTP would be at a higher temperature than that of the PPP. Furthermore if the inverse temperature transition (the increase in intramolecular order) is required for the development of elastomeric force, then the temperature dependence of elastomeric force of the PTP matrix would be expected to show a similar shift to higher temperature relative to that of the PPP matrix.

This inverse temperature transition is actually centered at near 50° C. for PTP, shifted some 25° C. higher than that of PPP. For Ile$^1$-PTP, it is shifted some 40° C. lower in temperature than that of PTP. Also, it has been found that the development of elastomeric force upon raising the temperature is similarly shifted about 25° C. higher for the PTP matrix (20 Mrad cross-linked) as compared to the PPP matrix (20 Mrad cross-linked).

Accordingly, in view of the above, it is possible, by selecting the appropriate combination of PTP and PPP matrices or analogs thereof to shift the transition temperature of a bioelastomer containing elastin PTP, PPP and analogs thereof and PHP over a range of about 75° C. Furthermore, wherever this transition would occur in the range of about $-25°$ C. for about 50% Phe$^1$-PPP in water/ethylene glycol or about 50° C. for PTP, in water, for example, there is a large change in elastomeric force which accompanies a relatively small change in temperature.

Thus, bioelastomers are available having incorporated therein repeating units having decreased hydrophobicity, such as —(VPGG)$_n$—or —(VPGAG)—$_n$.

For example, bioelastomers were provided containing elastomeric units comprising tetrapeptide, or pentapeptide or units thereof modified by hexapeptide repeating units and mixtures thereof, wherein the repeating units comprise amino acid residues selected from the group consisting of hydrophobic amino acid and glycine residues, wherein said repeating units exist in a conformation having a β-turn which comprises a tetrapeptide of the formula:

—X$^3$—(VPGG)$_n$—Y$^3$— wherein
X$^3$ is PGG, GG, G or a covalent bond;
Y$^3$ is VPG, VP, V or a covalent bond; and
V is a peptide-producing residue of L-valine;
P is a peptide-producing residue of L-proline; and
G is a peptide-producing residue of glycine; and n is an integer from 1 to 5,000, or n is 0, with the proviso that X$^3$ and Y$^3$ together constitute a repeating tetrameric unit in an amount sufficient to adjust the development of elastomeric force of the bioelastomer to a predetermined temperature.

Moreover, bioelastomers were provided containing elastomeric units comprising tetrapeptide, or pentapeptide or units thereof modified-by hexapeptide repeating units and mixtures thereof, wherein the repeating unit comprises amino acid residues selected from the group consisting of hydrophobic amino acid and glycine residues, wherein said repeating units exist in a conformation having a β-turn which comprises (A) a polypentapeptide of the formula:

—X$_1$—(IPGVG)$_n$—Y$^1$— wherein X$^1$, Y$^1$, P, G, I, V and n are as defined above; and (B) a polypentapeptide of the formula:

—X$^2$—(VPGVG)—$_n$Y$^2$—or
—X$^2$—(VPGAG)—$_n$Y$^2$— wherein X$^2$, Y$^2$, P, G, V, A and n are as defined above; or (C) a polytetrapeptide of the formula:

—X$^3$—(VPGG)$_n$—Y$^3$—or —X$^3$—(FPGG)—$_n$Y$^3$— wherein X$^3$, Y$^3$, P, G, V, F and n are as defined above, and F is phenylalanine, in relative amounts sufficient to adjust the development of elastomeric force of said bioelastomer to a predetermined temperature.

Thus, any PTP-analog can be used in the preparation of bioelastomers which suffices to attenuate the hydrophobicity of the functional repeating unit, such as +IPGG+ and +FPGG+ while retaining the elasticity of the bioelastomer.

Thus, bioelastomers are provided containing elastomeric units comprising tetrapeptide, or pentapeptide or units thereof modified by hexapeptide repeating units and mixtures thereof, wherein the repeating units comprise hydrophobic amino acid and glycine residues, wherein the repeating units exist in a conformation having a β-turn which comprises a tetrapeptide of the formula:

—X$^4$—(IPGG)$_n$—Y$^4$— wherein
X$^4$ is PGG, GG, G or a covalent bond;
Y$^4$ is IPG, IP, I or a covalent bond; and
I is a peptide-producing residue of L-isoleucine;
P is a peptide-producing residue of L-proline; and
G is a peptide-producing residue of glycine;
and n is an integer from 1 to 5,000, or n is 0, with the proviso that X$^4$ and Y$^4$ together constitute a repeating tetrameric unit, in an amount sufficient to adjust the temperature of which the elastomeric force of the bioelastomer develops.

Also provided are bioelastomers having the above-recited structural features, but which have any combination of the repeating units +IPGVG+$_n$, +VPGVG+$_n$, +VPGAG+$_n$, +VPGG+$_n$, +IPGG+$_n$, or other analogs thereof, such as Ala$^3$-PPP or Phe$^1$-PPP.

In fact, the present invention may include, in addition to polynonapeptides, in general, all bioelastomers containing elastomeric units comprising tetrapeptide, or pentapeptide or units thereof modified by hexapeptide repeating units and mixtures thereof, wherein the repeating units comprise hydrophobic amino acid residues and glycine residues, wherein the repeating units exist in a conformation having a β-turn which comprises a tetrapeptide or pentapeptide unit or repeating unit thereof, in an amount sufficient to adjust the development of elastomeric force at fixed length of said bioelastomer to a predetermined temperature, with the proviso that the elasticity of the bioelastomer is retained.

The following Examples and discussion are provided to exemplify the preparation of PTP. Of course, the Examples are for purposes of illustration only and are not intended to limit the present invention.

EXAMPLES

Peptide Synthesis

General Approach: The synthesis of polytetrapeptide, (VPGG)$_n$, can be achieved using any of the following permutations as the starting tetramer unit: Val-Pro-Gly-Gly, Gly-Val-Pro-Gly, Gly-Gly-Val-Pro, or Pro-Gly-Gly-Val. The first sequence (VPGG) was used in this laboratory both with the pentachlorophenyl ester (OPcp) activation and with the p-nitrophenyl ester (ONp) activation methods, and the latter method yielded polymer of significantly higher molecular weight. The sequence (GVPG) was utilized with -OPcp activation but no mention was made about the size of the polymer. In synthesizing the polypentapeptide, (VPGVG)$_n$, using different permutations of the pentamer unit with different activating groups for polymerization, it was observed that the pentamer having Pro as the C-terminal amino acid and -Onp for activation gave high molecular weight polymers. Similar results have been experienced in the case of the preparation of polyhexapeptide, (VAPGVG)$_n$. Hence, a similar approach was determined to be reasonable in the case of PTP also, i.e., sequence (GGVP) with -ONp activation. For comparison, H-VPGG-ONp, H-GVPG-ONp and H-GGVP-ONp were all tried for polymerization. As expected, the latter tetramer sequence gave a very high molecular weight polymer when determined by the TPI studies and here is described the synthesis of this latter material as shown in the Scheme II. The sequence (PGGV) wa not attempted because it has an optically active and bulky amino acid, Val, at its C-terminal.

Scheme II
Synthesis of H—(Gly—Gly—Val—Pro)$_n$—OH

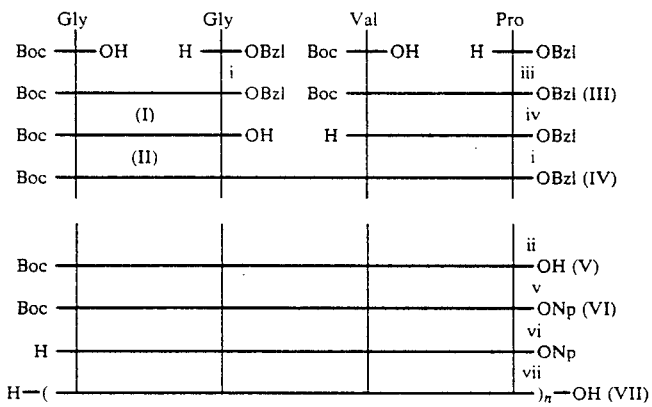

(i) EDCI/HOBt;
(ii) H$_2$—Pd/C;
(iii) IBCF—HOBt;
(iv) HCl/Dioxane
(v) Bis(p-nitrophenyl)carbonate;
(vi) TFA;
(vii) DMSO—NMM Boc-GG-OBzl (I) was prepared using EDCI for coupling and was hydrogenated to give acid (II). Boc-VP-OBzl (III) was synthesized by the mixed anhydride method in the presence of HOBt, deblocked, and coupled with II using EDCI-HOBt to obtain Boc-GGVP-OBzl (IV). After hydrogenating to the acid, V, it was converted to -ONp (VI) by reacting with bis(p-nitrophenyl)carbonate. After removing the Boc-group, the active ester was polymerized, dialyzed against water using a 50,000 molecular weight cut-off dialysis tubing and lyophilized. The intermediate and the final products were checked by carbon-13 nuclear magnetic resonance, thin-layer chromatography (TLC) and elemental analyses.

Details of Syntheses: Valine and Proline are of L'configuration. Boc-amino acids were purchased from Bachem, Inc., Torrance, Calif. HOBt was obtained from Aldrich Chemical Co., Milwaukee, Wis., and Bio-sil silica gel (200-400 mesh) was purchased from Bio-Rad Laboratories, Richmond, Calif. TLC plates were obtained from Whatman, Inc., Clifton, N.J. and the following solvent systems were used for determining the homogeneity of the products: $R_f^1$, CHCl$_3$(C):MeOH (M):CH$_3$COOH (A), 95:5:3, $R_f^2$, CMA (85:15:3); $R_f^3$, CMA (75:25:3); $R_f^4$, CM (5:1). Elemental analyses were carried out by Mic Anal, Tuscon, Ariz. Melting points were determined with a Thomas Hoover melting point apparatus and are uncorrected.

Boc-Gly-Gly-OBzl (I): Boc-Gly-OH (17.52 g, 0.1 mole) in a mixture of CHCl$_3$ (50 ml) and acetonitrile (50 ml) was cooled to $-15°$ C. and EDCI (19.17 g, 0.1 mole) was added and stirred for 20 minutes. To this, a pre-cooled solution of H-Gly-OBzl.tosylate (37.1 g, 0.11 mole), NMM (12.09 ml, 0.11 mole) in CHCl$_3$ (100 ml) was added and stirred overnight at room temperature. After removing the solvent, the residue was taken in CHCl$_3$ and extracted with acid and base. Chloroform was removed under reduced pressure, triturated with pet. obtain 30.2 g of I (yield: 93.7%), m.p. 82°-83° C. $R_f^2$, 0.52; $R_f^4$, 0.82. Anal. Cald. for C$_{16}$H$_{22}$N$_2$O$_5$: C, 59.61; H, 6.88, N, 8.69%. Found: C, 59.43; H, 6.88; N, 8.35%.

Boc-Gly-Gly-OH (II): I (10 g, 0.31 mole) in acetic acid (100 ml) was hydrogenated at 40 psi in the presence of 10% Pd-C catalyst (1 g). The catalyst was filtered with the aid of celite and solvent removed under reduced pressure. The residue was triturated with EtOAC, filtered, washed with EtOAC, pet. ether and dried to yield 6.3 g of II (yield: 87.5%), m.p. 118°-120° C. (decomp.). $R_f^2$, 0.28; $R_f^3$, 0.44. Anal. Calcd. for C$_9$H$_{16}$N$_2$O$_5$H$_2$O: C, 43.19; H, 7.25; N, 11.19%. Found; C, 43.53; H, 7.40; N 10.90%

Boc-Gly-Gly-Val-Pro-OBzl (IV): III (6.0 g, 0.0148 mole) was deblocked with HCl/Dioxane and solvent removed under reduced pressure. The residue was triturated with ether, filtered, washed with ether, then pet. ether and dried. A very hygroscopic material was obtained (4.2 g, 0.0123 mole) which was coupled in DMF with II (2.86 g, 0.0123 mole) in the presence of 10% excess of EDCI (2.60 g) and HOBt (2.07 g). The reaction was worked up as described for I to obtain IV as a white foam in a quantitative yield, no sharp m.p. 54°-62° C. $R_f^2$, 0.42, $R_f^3$, 0.74. Anal Calcd. for C$_{26}$H$_{38}$N$_4$)$_7$; C, 60.21; H, 7.38; N, 10.805. Found: C, 60.0; H, 7.46; N, 10.81%.

Boc-Gly-Gly-Val-Pro-OH (V): IV (6.2 g, 0.012 mole) in acetic acid was hydrogenated and worked up as for II to obtain V quantitatively, no sharp m.p. 743 Calcd. for 83° C. $R_f^3$, 0.25; $R_f^4$, 0.15. Anal. Calcd. for C$_{19}$H$_{32}$N$_4$O$_7$: C, 51.10; H, 7.67; N, 12.54%. Found: C, 51.28: H, 7.50, N, 12.38%.

Boc-Gly-Gly-Val-Pro-ONp (VI): V (5.3 g, 0.0123 mole) in pyridine (30 ml) was reacted with bis(pnitrophenyl)carbonate (5.64 g, 0.0185 mole). After removing the solvent, the residue was taken in CHCl$_3$ and extracted with acid and base. The peptide was chromatographed over a silica-gel column and eluted with 35% acetone in CHCl$_3$ after initially eluting with CHCl$_3$' to obtain 4.7 g of VI (yield: 69.2%), no sharp 74°-79° C. $R_f^2$, 0.76; $R_f^4$, 0.75. Anal. Calcd. for C$_{25}$H$_{35}$N$_5$O$_9$.1/2-

H₂O: C, 53/75 H, 6.49; N, 12.53%. Found: C, 53.69; H, 6.44; N, 12.34%.

H-(Gly-Gly-Val-Pro)$_n$-OH (VII): VI (4.5 g, 0.0082 mole) in CHCl₃ (20 ml) was treated with TFA (35 ml) for 30 minutes and solvent removed under reduced pressure. The residue was triturated with ether, filtered, washed with ether, then with pet. ether and dried. The TFA salt (3.9 g, 0.0069 mole) in DMSO (7.6 ml) and NMM (1.22 ml, 1.6 equiv) was stirred for 14 days. After diluting with cold water, the polymer was dialyzed in a 50 kD cut-off dialysis tubing, changing water daily for 15 days, and the retentate was lyophilyzed to yield 1.65 g of the polytetrapeptide (yield: 77%). The carbon-13 NMR spectrum has been determined. The assignments have all been made and there were no extraneous peaks thereby verifying the synthesis.

Attention is here directed to the remarks made above regarding the use of microbial biosynthesis for the preparation of the present bioelastomers.

Temperature Profiles for Coacervation

Polypeptide coacervation in water is reversible aggregation to form a new phase with a distinct composition. Association occurs on raising the temperature, disassociation on lowering the temperature. The process of coacervation was followed by monitoring the turbidity as a function of temperature using a Cary 14 spectrophotometer set at 300 nm, a Neslab ETP-3 temperature programmer with a 30° C./hour scan rate and an Omega 199A thermocouple monitor. The sample cell was placed in a vibrating chamber (300 Hz) to keep the aggregates from settling and to facilitate equilibrium. The temperature profiles for coacervation are concentration dependent. Dilution from a high concentration, after the high concentration limit is reached (approximately 40 mg/ml for high molecular weight elastomeric polypeptides), results in a shift of the turbidity profile to higher temperature.

Circular Dichroism Measurements

A Cary 60 spectropolarimeter equipped with a Model 6001 circular dichroism accessory with 330 Hz modulation of the left and right circular polarized beams was used to determine the circular dichroism patterns of 5 mg PTP in one ml of deionized-distilled (quartz immersion heater) water. Because of the smaller size or the relative transparency of the PTP aggregates (as with the cross-linked PTP matrix with a relatively small change in refractive index between solution and matrix) when compared to that of the PPP system, it was possible to use the 5 mg/ml concentration for the CD studies without being compromised by light scattering (particulate) distortions of the CD spectra. This is apparent from monitoring the negative band near 220 nm which becomes damped and red-shifted as the particulate distortions become significant.

Preparation of the Cross-linked PTP Matrix

The PTP was prepared for γ-irradiation cross-linking by dissolving 130 milligrams of th peptide in 220 milligrams of water in a cryotube. The material was shear oriented overnight at 40° C. in a previously described pestle-cryotube assembly. The sample was exposed to approximately 8,000 Roentgen/min γ-irradiation at the Auburn University Nuclear Science Center. Exposure was of sufficient time to achieve a 20 × 10⁶ radiation absorbed dose (20 Mrad).

Thermoelasticity Measurements

Thermoelasticity studies were carried out on a stress-strain apparatus. Clamping of the sample in the holder was done in two stages to prevent damage to the material at the clamp edge. The sample was first gripped lightly with the top clamp, raised to 60° C. while submerged in water within the temperature jacket and allowed to equilibrate for about 2 hours. The measured force consisting of the weight of the sample and grips in water were set to zero. The bottom grip was then attached to the sample and both grips tightened to hold the sample firmly. The bottom clamp was driven as in a stress-strain measurement and stopped at 40% elongation. Force data were recorded in 5° C. steps starting at 70° C. and continuing to 40° C. where the force approached zero.

RESULT

Temperature Profiles for Coacervation

The polytetrapeptide is soluble in water in all proportions below 40° C. On raising the temperature above 40° C. the solution becomes turbid; on standing settling occurs to form a dense viscoelastic phase called a coacervate. The process is readily reversible; on lowering the temperature cloudiness clears and coacervate readily redissolves. By following the turbidity as a function of temperature, temperature profiles for coaverva- tion are obtained which are concentration dependent. As more concentrated solutions are used, the onset of turbidity occurs at lower temperatures until further increases of concentration cause no further lowering of the temperature for onset of turbidity. The lower concentration above which raising the concentration no further lowers the temperature for onset of turbidity is called the high concentration limit. For this high molecular weight PTP the high concentration limit is 40 mg/ml as 100 mg/ml gives the same profile. Dilution from 40 mg/ml causes a shift to higher temperature for the onset. are compared to similar data for the PPP. The midpoint for the high concentration limit of PTP is 49° C. whereas the value for the high concentration limit of PPP is 25° C. The decreased hydrophobicity of the tetramer results in a 24° C. increase in the temperature required to bring about the hydrophobic interactions attending aggregation.

Circular Dichroism

At the lower temperature there is a negative band near 220 nm and a second negative band in the 195–200 nm range. This latter band is considered to be indicative of polypeptides with limited order as fully disordered polypeptides are considered to have a negative band near 195 nm with an ellipticity of $-4 \times 10^4$. The lower magnitude of the short wavelength negative band for PTP and the negative band near 220 nm indicate some order in the PTP at 35° C. On raising the temperature the short wavelength negative band decreases in magnitude indicative of a transition toward greater intramolecular order. Interestingly, its midpoint corresponds approximately to the midpoint in the temperature profile for coacervation for a comparable concentration. It is important to note for the PTP that the change in intramolecular order precedes the intermolecular interactions, i.e., begins at a substantially lower temperature than the aggregational process. The temperature midpoint for the PTP intramolecular transition is shifted some 25° C. to higher temperatures from that of the PPP. Thus, the intramolecular ordering of the PTP is shifted to higher temperature due to the decreased hydrophobicity of the tetramer as compared to the pentamer.

Thermoelasticity Data

The temperature dependence of elastomeric force (thermoelasticity data) is plotted in FIG. 8B for 20 Mrad cross-linked PTP at an extension of 40%. There is very little elastomeric force exhibited by this matrix below 40° C. As the temperature is raised above 40° C., however, the elastomeric force develops to a maximal value near 70° C. Also included for comparison in FIG. 8B are the thermoelasticity data for a 20 Mrad cross-linked PPP matrix which exhibit a similar transition but shifted some 20° to 25° C. to lower temperatures. The development of elastomeric force, just as the temperature dependence of coacervation and of ellipticity for the PTP, is shifted by about 25° C. from that of the PPP. These properties are a function of the hydrophobicity of the repeating unit. Of particular interest is the comparison of the ellipticity data for the PTP with the thermoelasticity for the PTP. The transition as followed by ellipticity, which is a measure of intramolecular order, begins in the range 35° to 40° C., and similarly the elastomeric force begins, to develop just below 40° C. By both physical measurements the transition is essentially complete by 70° C. There is a close parallel between-increase in intramolecular order and increase in elastomeric force. As the aggregational intermolecular processes, followed by turbidity, do not become significantly until nearly 50° C., it appears that the PTP matrix allows a delineation between intramolecular and intermolecular processes as related to origins of elastomeric force.

The bioelastomeric materials of the present invention exhibit an inverse temperature transition resulting in the development of a regular non-random structure, unlike typical rubbers, which utilize, as a characteristic component, hydrophobic intramolecular interactions. The regular structure appears to be a β-spiral, a loose water-containing helical structure with β-turns as spacers between turns of the helix which provides hydrophobic contacts between helical turns and has suspended peptide segments. These peptide segments are relatively free to undergo large amplitude, low frequency rocking motions called liberations. This produces the librational entropy mechanism of elasticity.

An essential feature of the elastomeric pentapeptide, tetrapeptide, hexapeptide and nonapeptide-containing elastomeric units of the present invention is the existence of a sequence of regularly recurring β-turns in the protein's secondary structure, i.e., the conformation of its peptide chain. A β-turn is characterized by a ten atom hydrogen bonded ring of the following formula showing residues i, i+1, i+2 and i+3:

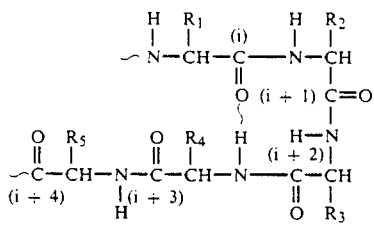

In this formula, $R_1$–$R_5$ represent the side groups of the respective amino residues. Notably, $R^5$ of (i+4) can also be i' of a subsequent β-turn. Likewise, subsequent residues (i+1)', (i+2)' and (i+3)' are analogous and as defined for residues i, i+1, i+2 and i+3 of the first β-turn.

The spiral structures produced by a series of β-turns are more open than the more common α-helix. As a result, the atoms between the atoms that participate in hydrogen bonding have a relatively greater freedom of movement, more so than in an α-helix. This is particularly true of librational motions involving peptide moieties. A libration is a torsional oscillation involving simultaneous rotational motions of the two single bonds on each side of a librating moiety. The moiety involved in a libration may be a single peptide bond or several peptide residues. For adequate freedom of motion to exist, it is important, however, that the carbonyl oxygen and that amino hydrogen of the peptide bond not be involved in a motional restricting hydrogen bonding to other parts of the molecule or to other peptide molecules. Otherwise a greater energy barrier to the libration exists and motion will be restricted. Since non-hydrogen-bonded segments having freedom of motion exist in the β-spiral between the points of hydrogen bonding for the β-turns, these segments may be said to be librationally suspended with librational capabilities. Librationally active suspended segments associated with glycine resides are, therefore, a necessary structural feature that exists in the elastomeric polymer between the repeating β-turns.

Another factor leading to the high librational freedom of such molecules is the absence of polar interactions between the amino acid residues, either interchain or interchain, other than the previously mentioned hydrogen bond. The amino acid residues present are generally all hydrophobic or glycine and accordingly do not exert significant forces on one another through space. If charged or polar groups are present, electrostatic interactions would limit librational freedom and restrict the number of available states in the related (non-extended) form of the molecules. Polar and charged amino acid residues are not strictly prohibited, however, if their presence does not destroy the elasticity of the polypeptide molecule as a whole. For example, an occasional serine residue is present in the polypentapeptide sequence of naturally occurring porcine tropoelastin without destroying elasticity. Accordingly, hydrophobic amino acid residues and glycine are preferred in forming elastomeric polypeptides of the present type although other amino acids may be present to a small extent.

The size of the repeating unit of the elastomeric component is important in determining the stability and dynamic properties of the β-spiral. Repeating units having fewer than four or more than five amino acid residues do not easily form β-spirals having the required librational motions. Three amino acid residues are too few for both a β-turn and a dynamic suspended segment.

For the PTP, the dynamic segment is simply the residue 4- residue 1 bridging peptide moiety. Further, for the PPP, the dynamic segment includes both peptde moieties flanking the fifth residue. We now describe elastomeric repeats wherein the dynamic segments involve entire pentameric, tetrameric or trimeric bridging segments. Clearly the key elements are structural hydrophobic spacers, e.g., the β-turn, between which are segments capable of dynamic motion wherein the dynamic motion becomes of lower amplitude upon chain extension.

In the specific case of the polynonapeptide it can be a combination of two $\beta$-turns, the common $\beta$-turn with Pro$^2$-Gly$^3$ as residues i+1 and i+2, and an additional $\beta$-turn with Val$^6$-Gly$^7$ as residues (i+1)' and (i+2)'. In this case, the dynamic suspended segment is best defined as the Ala$^8$-Gly$^9$-Val$^1$ segment or the Val$^8$-Gly$^9$-Val$^1$ segment by direct analogy to the Val$^4$-Gly$^5$-Val$^1$ suspended segment of poly(VPGVG).

The choice of individual amino acids from which to synthesize the bridging sections of the elastomeric repeating units and resulting polypeptide is unrestricted so long as the resulting structure comprises librationally suspended segments in a $\beta$-spiral. The amino acids are not restricted to $\alpha$-amino acids, although these are preferred since it has recently become possible to predict the occurrence of $\beta$-turns from the $\alpha$-amino acid sequence of a polypeptide A review article discussing the prediction of protein conformation, including the prediction of $\beta$-turns, was published by Chou and Fasman, *Ann. Rev. Biochem.*, 47, 251 (1978), which is herein incorporated by reference. The size of the side chains present in the hydrophobic amino acids does not greatly affect the $\beta$-spiral since the side chains generally extend outward from the surface of the spiral with some important but non-restrictive interturn hydrophobic interactions. However, in order to minimize interchain interactions, it is preferred that the side chain contain no more than 10 carbon atoms. Preferred hydrophobic side chains are the same as those previously described for position $\delta$, which is position i+3. In addition, it appears from the studies leading to the present invention that preferred side chains of the amino acids are hydrogen or hydrocarbon chains having 1-4 carbon atoms. Examples of especially preferred residues are glycine and the naturally occuring L-amino acids alanine, valine, leucine, and isoleucine as well as closely related molecules such as 2-methyl-2-aminopropanoic acid, L-2-aminobutanoic acid, and L-2-methyl-2-aminobutanoic acid, although it is preferred that the $\alpha$-carbon have an $\alpha$-hydrogen. Proline is also a preferred amino acid.

It is also possible to use $\alpha$-hydroxy acids, such as $\alpha$-hydroxy-isovaleric acid or even glycolic acid, at any positions except position 4, which are positions i+3 and (i+3)' which are $\delta$ and $\pi$, respectively.

For clarity, the sequence:

$(\alpha\beta\gamma\delta\epsilon\theta\lambda\pi\rho)$ is numbered such that $\alpha$ is position i, $\beta$ is position i+1, $\gamma$ is position i+2 and $\delta$ is position i+3. $\epsilon,\theta,\lambda,\pi$ and $\rho$ might then be considered positions i+4, i+5, i+6, i+7 and i+8, respectively. For the subsequent $\beta$-turn, i+4 is i', i+5 is (i+1)', i+6 is (i+2)', and i+7 is (i+3)'. This numbering sequence is also used above in the illustration of the $\beta$-turn in order to show the residues which are important in the $\beta$-turn formation. However, in accordance with the present invention, each of the above residues, i.e, $\alpha$ through $\rho$ may be a variety of peptide-forming residues as will now be discussed.

$\alpha$ is generally any L-hydrophobic peptide-forming residue. However, $\alpha$ is generally L-Valine or another peptide-forming residue capable of functioning in position i of a $\beta$-turn in a polypeptide. By the term "capable of functioning in position i" is meant peptide-forming residues of L-Valine, L-isoleucine, L-leucine, L-phenylalanine, L-tryptophan and L-tryosine, for example. L-Valine, however, is a preferred such peptide-forming residue.

$\beta$ is generally also any L-hydrophobic peptide-forming residue. However, $\beta$ is generally L-Proline or another peptide-forming residue capable of functioning in position i+1 of a $\beta$-turn in a polypeptide. By the term "capable of functioning in position i+1" is meant peptide-forming residues of L-Proline and residues which sterically constrain the peptide-bond torsion angle. These may be the same residues as defined for $\alpha$. Such residues are, for example, L-Valine, L-isoleucine, L-leucine, L-phenylalanine, L-tryptophan and L-tyrosine, L-Proline, however, is a preferred such peptide-forming residue.

$\gamma$ is any hydrophobic peptide-forming residue which has a relatively small steric requirement $\gamma$ is generally Glycine, however other peptide-forming residues capable of functioning in position i+2 of a $\beta$-turn in a polypeptide may be used. By the term "capable of functioning in position i+2" is meant peptide-forming residues of Glycine, D-alanine, L-alanine, D-valine, D-isoleucine, D-leucine, D-phenylalanine, D-tryptophan and D-tyrosine. Other residues of similar steric requirements may also be used. The only exception appears to be L-hydrophobic residues other than glycine and L-alanine which appear to interfere with $\beta$-turn formation. However, it is preferred that $\gamma$ is glycine.

$\delta$ is generally any L-hydrophobic peptide-forming residue. However, $\delta$ is generally as defined above for $\alpha$. Thus, by the term "capable of functioning in position i+3" is meant peptide-forming residues of L-valine, L-isoleucine, L-leucine, L-phenylalanine, L-tryptophan and L-tyrosine, for example. It is preferred that $\delta$ is L-phenylalanine or L-leucine.

$\epsilon$ is generally any hydrophobic peptide-forming residue of small steric requirements. In this case, generally $\epsilon$ is a peptide-forming residue of Glycine or D-alanine. $\epsilon$ is preferably Glycine.

However, $\epsilon$ may also be a hydrophobic peptide-forming residue of large steric requirement as defined above for $\alpha$, in which case $\delta$ is necessarily a hydrophobic peptide-residue of small steric requirement as defined above for $\epsilon$. In this case, $\delta$ is then as defined for $\epsilon$, i.e., a peptide-forming residue of Glycine or D-alanine.

For the subsequent $\beta$-turn, $\epsilon$ is position i', and $\theta$, $\lambda$, and $\pi$ are positions (i+1)', (i+2)' and (i+3)'.

When $\epsilon$ functions as position i' of the subsequent $\beta$-turn in the polypeptide, it may be Glycine or D-alanine when $\delta$ is as defined above. Alternatively, $\epsilon$ may be defined as $\alpha$, when $\delta$ is Glycine or D-ala.

$\theta$ is generally any L-hydrophobic peptide-forming residue. However, generally $\theta$ is a peptide-forming residue such as L-valine, L-alanine, or as defined above for $\alpha$. Alternatively, when $\theta$ functions as position (i+1)' of a subsequent $\beta$-turn in a polypeptide, $\theta$ may also be a peptide-forming residue as defined above for $\beta$.

$\lambda$ is generally Glycine or any peptide-forming residue as defined above for $\gamma$ or such a residue of D-alanine. Notably, when $\lambda$ functions as position (i+2)' of a subsequent $\beta$-turn in a polypeptide, $\lambda$ is as defined above for $\gamma$.

$\pi$ is a generally any L-hydrophobic peptide-forming residue. However, it is preferably such a residue of L-valine or L-alanine or such a residue as defined for $\alpha$. However, $\pi$ may also be a direct bond. If $\pi$ is a direct bond, octameric sequences are described. One specific case of —(VPGG)— or —(VPGGVPGG)— has already been described in issued U.S. patents.

Finally, ρ is either glycine or D-alanine.

Notably moieties X and Y are as defined above. However, a further proviso to the defined sequences is that for residues ε, θ, λ, π and ρ no more than three of the same should be glycine simultaneously.

However, in another principal aspect of the present invention are provided polynonapeptides having an increased elastic modules and which exhibit chemotoxis toward fibroblastics and endothelial cells. When chemotaxis is also required, it is important that either of the pentameric sequences —(GFGVG)— or —(GLGVG)— be incorporated as five of the nine residues are preferably linked sequentially in the peptide sequence.

Inasmuch as residue π be a direct bond, the present invention also specifically contemplates octameric sequences. However, the same rules noted above for nonameric sequenes will also apply to the octameric sequences when designing bioelastomeric sequences and such sequences which are also chemotactic.

As mentioned above, the present invention provides polynonapeptide and other elastomeric polypeptides containing nonapeptide sequences.

In accordance with the present invention, the present nonapeptide sequences, i.e., 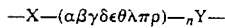
may be incorporated as only one unit, where n is 1, in any one of the elastomeric polypeptides disclosed above or as many repeating units where n is up to about 5,000 units. The repeating polynonapeptide units may be part of a "homopolymer" polynonapeptide where n may have a value of as high as 5,000, or the nonapeptide units may be interspersed throughout other elastomeric polypeptide units to form a copolymeric elastomer.

For example, the sequence:

—X—(αβγδεθλπρ)—$_n$Y— as defined above, may be incorporated as part of a repeating unit:

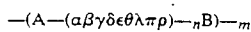

where A and B may be any of the elastomeric polypentapeptide or polytetrapeptide sequences described above, including those sequences incorporating any amino acid substitutions for the purpose of modifying the temperature of transition for the elastomer. In the above formula, both m and n have a value of 1 to about 5,000.

For example, A and B may be the same or different and may each represent unit or repeating sequences of PPP or PTP or —(IPGVG)— or —(IPGG)—, for example. A and B may represent random or block assemblages of any of the aforementioned elastomeric sequences.

Also, A and B may each represent repeating sequences of —(APGVGV)—, which are not elastic and which function to align polypeptide chains by an interlocking mechanism and which also function to modulate the elastic modulus.

It is also specifically contemplated by the present invention that the present nonapeptide and polynonapeptide sequences be used in conjunction with other elastomeric sequences, i.e., A and B, wherein the other elastomeric sequences have been modified for the purpose of attenuating the inverse temperature transition. Any of the above-described substitutions may be used and are herein considered to be within the definition of the terms "A" and "B". Thus, the moieties "A" and "B" are defined as elastomeric moieties which develop elastomeric force when at fixed length by an inverse temperature transition.

It is important to note that any elastomeric sequence disclosed herein may be used as moieties A and B. Any combination of the above-described PTP, PPP or PHP sequences or those sequences substituted to modulate the temperature of the inverse temperature transition may be used in order to set the overall elastic modulus at a desired value. The phrase "moiety which is capable of modulating elastomeric force by an inverse temperature transition" concisely defines moieties A and B as the present inventors are unaware of any other polymeric materials which so function.

Although PHP, as noted above, is not elastomeric, either moieties A or B may include such a sequence provided that the overall elastic modulus of the matrix is maintained at a desired value.

For example, moieties A and B may each be —APGVGV)$_m$, —VPGVG)$_m$, —IPGVG)$_m$, —VPGAG)$_m$, —VPGG$_m$, —IPGG)$_m$ and —FPGG)$_m$, wherein V, P, G, I, A and F are peptide-forming residues of the respective amino acids as defined by the standard one-letter abbreviations, and m has a value of from 1 to about 5,000.

Notably, all of the earlier above-described U.S. patents and pending patent applications are specifically incorporated herein by reference.

The polynonapeptide of the present invention, whether homopolymer or copolymeric in nature, may be easily synthesized according to the methods previously described for PTP and PPP.

Having now fully described the present invention, the same will now be more fully understood in view of the following examples which are provided solely for the purpose of illustration and are not intended to limit the present invention.

EXAMPLE

Peptide Synthesis: Elemental analyses were carried out by Desert Analytics, Tucson, Ariz. All amino acids were of the L-configuration. Thin layer chromatography (tlc) was performed on silica gel plates obtained from Whatman, Inc., New Jersey. tert-Butyloxycarbonyl (BOC)-amino acids and amino acid benzyl esters (-OBzl) were purchased from Bachem, Inc., Torrance, Calif.

The synthesis of the nonapeptide and its polymer was carried out by the classical solution methods and is presented in Scheme III. Briefly, the synthetic approach was to synthesize the tetrapeptide unit BOC-AGVP-OH and the pentapeptide unit H-GFGVG-OBzl and couple them together using 1-ethyl-3-dimethylaminopropyl carbodiimide (EDCI) and 1-hydroxybenzotriazole (HOBt) to obtain BOC-AGVPGFGVG-OBzl, which represents a different permutation of VPGFGVGAG. The former sequence was selected since it represents sterically hindered amino acids at the N-terminus as well as at the C-terminus for possibly enhancing polymerization yields. The tetra- and pentapeptides were synthesized using the mixed anhydride method, or the EDCI coupling method as described previously. The nonapeptide benzyl ester was hydrogenated to the free acid and converted to the p-nitrophenyl ester (—ONp) using bis(p-nitrophenyl) carbonate. The N$^α$Boc-group was removed, and the active ester was polymerized for 14 days in dimethylsulfoxide (DMSO) at a one molar concentration in the presence of 1.6 equiv. of N-methylmorpholine (NMM) as the base. After diluting with water, the polymer was transferred into a 3500 dalton cut-off dialysis tubing and dialyzed for one week changing water everyday. The polymer was lyophilized, treated with base, to remove any unreacted —ONp esters and redialyzed using a 50 kD cut-off dialysis tubing and lyophilized. The intermediate products and the final polymer were characterized by tlc, elemental analyses, carbon-13 and proton NMR spectroscopic methods.

solvent removed under reduced pressure. The residue was triturated with ether, filtered, washed with ether, petroleum ether and dried. The peptide was characterized and compared with the sample previously prepared by a different method.

BOC-Ala-Gly-Val-Pro-Gly-Phe-Gly-Val-Gly-ONp: After hydrogenating the above peptide benzyl ester, to produce the free acid, and amount of 7.5 g, 8.69 mmol in pyridine (100 ml) was treated with bis(p-nitrophenyl) carbonate (3.69 g, 13 mmol) for several days. Pyridine was removed under reduced pressure, triturated with ether, filtered washed with ether, petroleum ether and

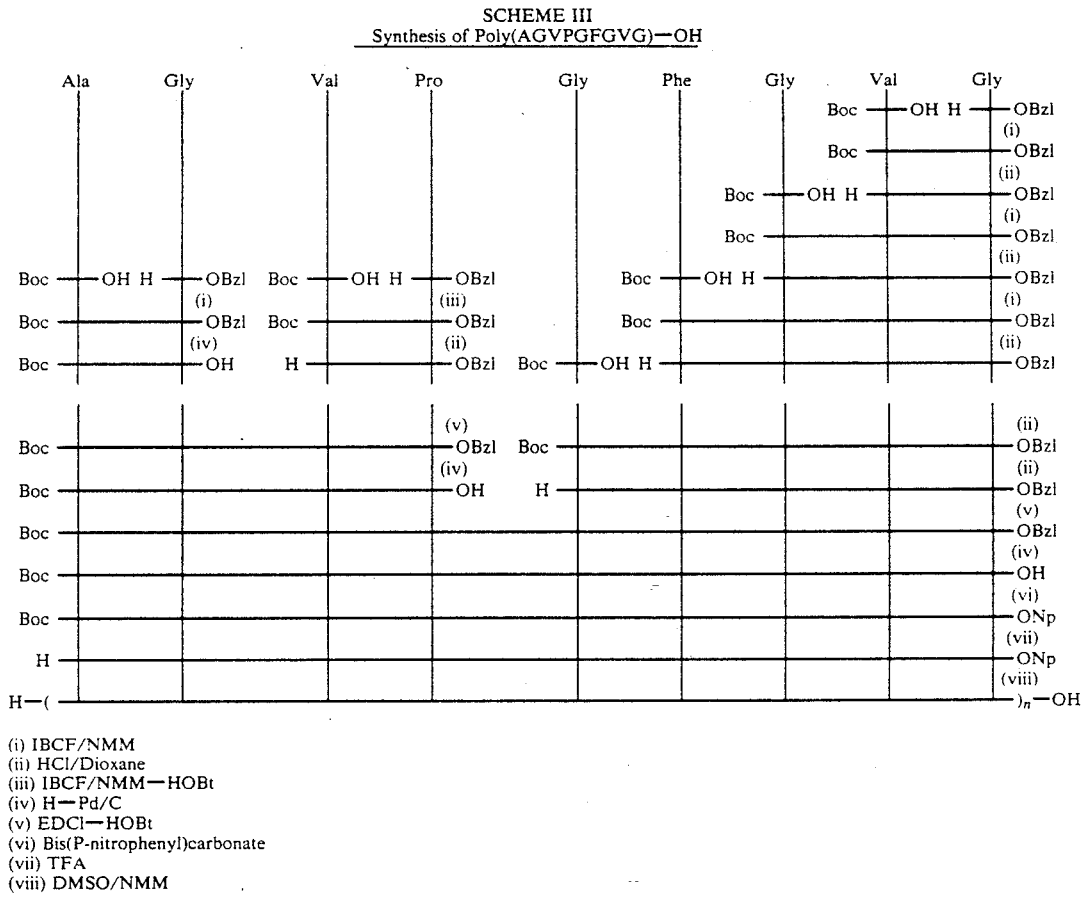

SCHEME III
Synthesis of Poly(AGVPGFGVG)—OH (i) IBCF/NMM
(ii) HCl/Dioxane
(iii) IBCF/NMM—HOBt
(iv) H—Pd/C
(v) EDCl—HOBt
(vi) Bis(P-nitrophenyl)carbonate
(vii) TFA
(viii) DMSO/NMM Abbreviations: Boc, tert-butyloxycarbonyl; OBzl, benzyl ester; DMF, dimethylformamide; DMSO, dimethylsulfoxide; EDCI, 1 ethyl-3-dimethylaminopropyl carbodiimide; HOBt, 1-hydroxybenzotriazole; IBCF, isobutylchloroformate; NMM, N-methylmorpholine; ONp, p-nitrophenyl ester; TFA, trifluoroacetic acid; A, alanine; G, glycine, F, phenylalanine; P, proline; V, valine.

BOC-Ala-Gly-Val-Pro-Gly-Phe-Gly-Val-Gly-OBzl: BOC-AGVP-(OH(5.26 g, 11.8 mmol) and HOBt (1.99 g, 13 mmol) were dissolved in dimethylformamide (35 ml) and cooled with ice-water. EDCI (2.49 g, 13 mmol) was added and stirred for 20 min. To this solution was then added an ice cold solution of HCl-H-GFGVG-OBzl (7.6 g, 11.8 mmol) and NMM (1.3 ml, 11.8 (mmol) in DMF (35 ml). The reaction mixture was stirred for 2 days at room temperature and the solvent was removed under reduced pressure. The residue was taken into CHCl$_3$ and extracted with water, 10% citric acid, water, 0.5N NaOH, water, dried over anhyd. Na$_2$SO$_4$ and dried to yield 7.3 g (yield: 85.38%) of the desired product. Further purification was carried out by silica gel column chromatography using 13% EtOH in CHC$_{l3}$. All of the fractions which showed single spots on tlc were pooled and concentrated. The R$_f$ in CHCl$_3$ (85): CH$_3$OH(15): HOAC(3) was 0.58. Anal. calcd. for C$_{46}$H$_{64}$N$_{10}$O$_{014}$.2H$_2$O, C, 54.15; H, 6.71; N, 13.73%. Found: C, 54.46; H, 6.48; N, 13.75%.

Poly[Ala-Gly-Val-Pro-Gly-Phe-Gly-Val-Gly]-OH: The

N$^\alpha$-BOC-group from the above peptide-ONp was removed by treatment with TFA for 45 min. TFA was evaporated under reduced pressure, triturated with ether, filtered, washed with ether and dried. The TFA salt (1.0 g, 1 mmol) was taken in DMSO (1 ml); NMM (0.18 ml, 1.6 equiv.) was added, and the sample was stirred for 14 days. After 4 days of stirring, the solution turned very viscous and 1.5 ml more of DMSO were added and stirring continued. The reaction mixture was diluted with water, transferred into dialysis tubing and dialyzed with frequent exchanges of bathing water for 10 days. The insoluble material in the tubing was treated with 1N NaOH overnight in the cold room, neutralized and redialyzed using a 50 kD cut-off dialysis tubing. The polymer was solubilized by lyophilizing from trifluoroethanol-water mixtures.

Nuclear Magnetic Resonance Verification of Synthesis: Both carbon-13 and proton nuclear magnetic resonance (NMR) spectra of poly(VPGFGVGAG) are given in FIGS. 1 and 2, respectively. The assignment of resonances are all indicated and these with the absence of extraneous peaks verify the synthesis and purity of the product.

Figure 3:
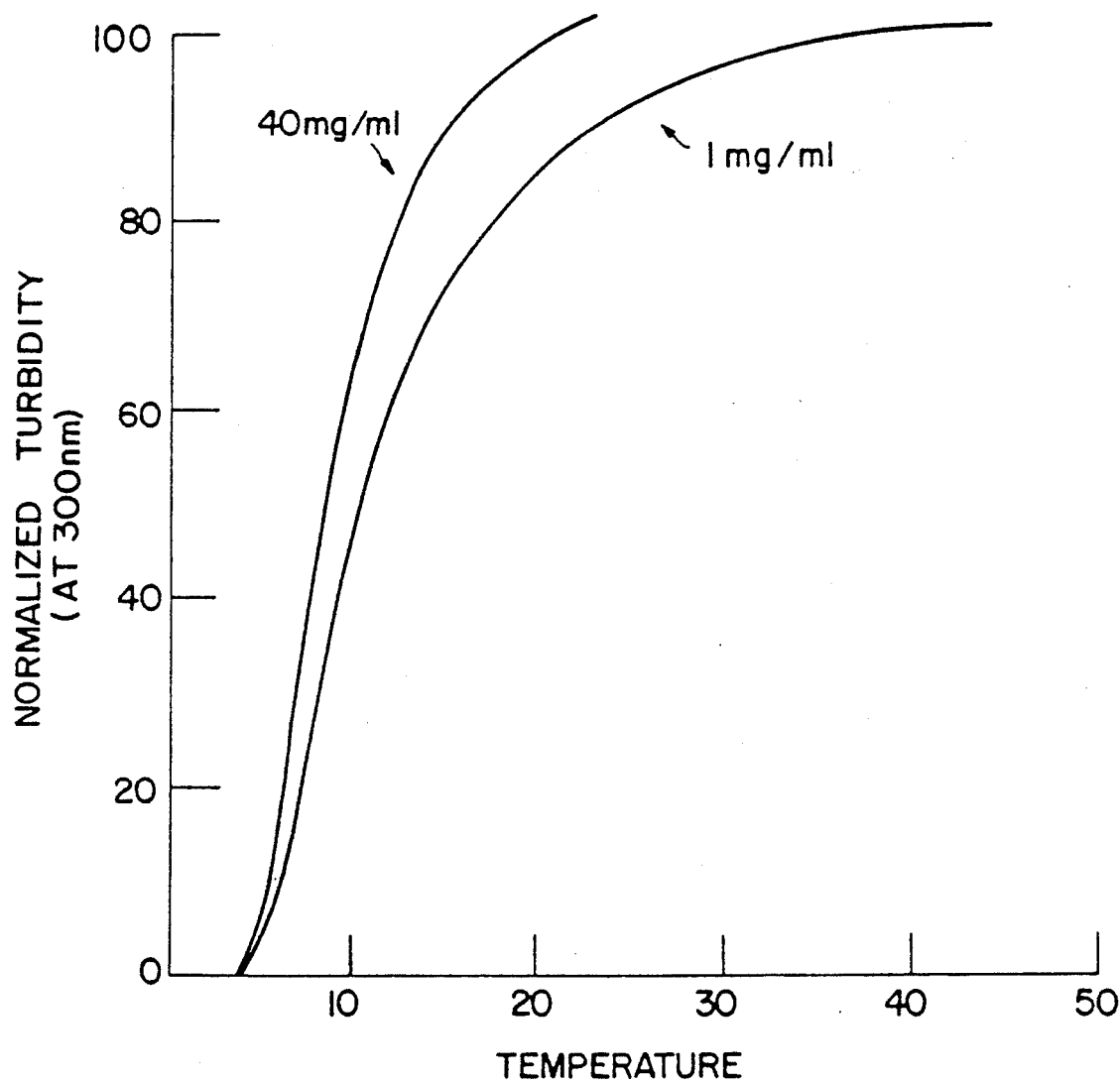
FIG. 3 illustrates temperature profiles of turbidity (TPτ) data for poly(VPGFGVGAG) at 40 mg/ml and 1 mg/ml concentrations in H$_2$O. The aggregational process was monitored by measuring light scattering at 300 nm as a function of temperature using a Cary 14 recording spectrophotometer.

Formation of Insoluble Matrices: The polynonapeptide, poly(VPGFGVGAG), can be solubilized in water below 5° C. On raising the temperature, the solution becomes cloudy as shown in the temperature profiles for turbidity development (aggregation) in FIG. 3 for 40 mg/ml and 1 mg/ml solutions. As the aggregates grow in size, they settle out to form a viscoelastic phase. When the viscoelastic phase is collected in a tube and a pestle with a channel cut in it is inserted into the tube, the viscoelastic phase flows into and fills the channel On $\gamma$-irradiation with a $20 \times 10^6$ radiation absorbed dose (20 Mrad) from a Cobalt-60 source, a cross-linked elastomeric matrix is produced which is suitable for mechanical studies. The resulting matrix is referred to as $X^{20}$-PNP or $X^{20}$-poly(VPGFGVGAG).

Stress/Strain Studies: The stress/strain studies were performed on an apparatus built in this laboratory as previously described with the exception that a Sensotec Model 31 force transducer was used allowing force levels up to 250 grams.

Figure 2:
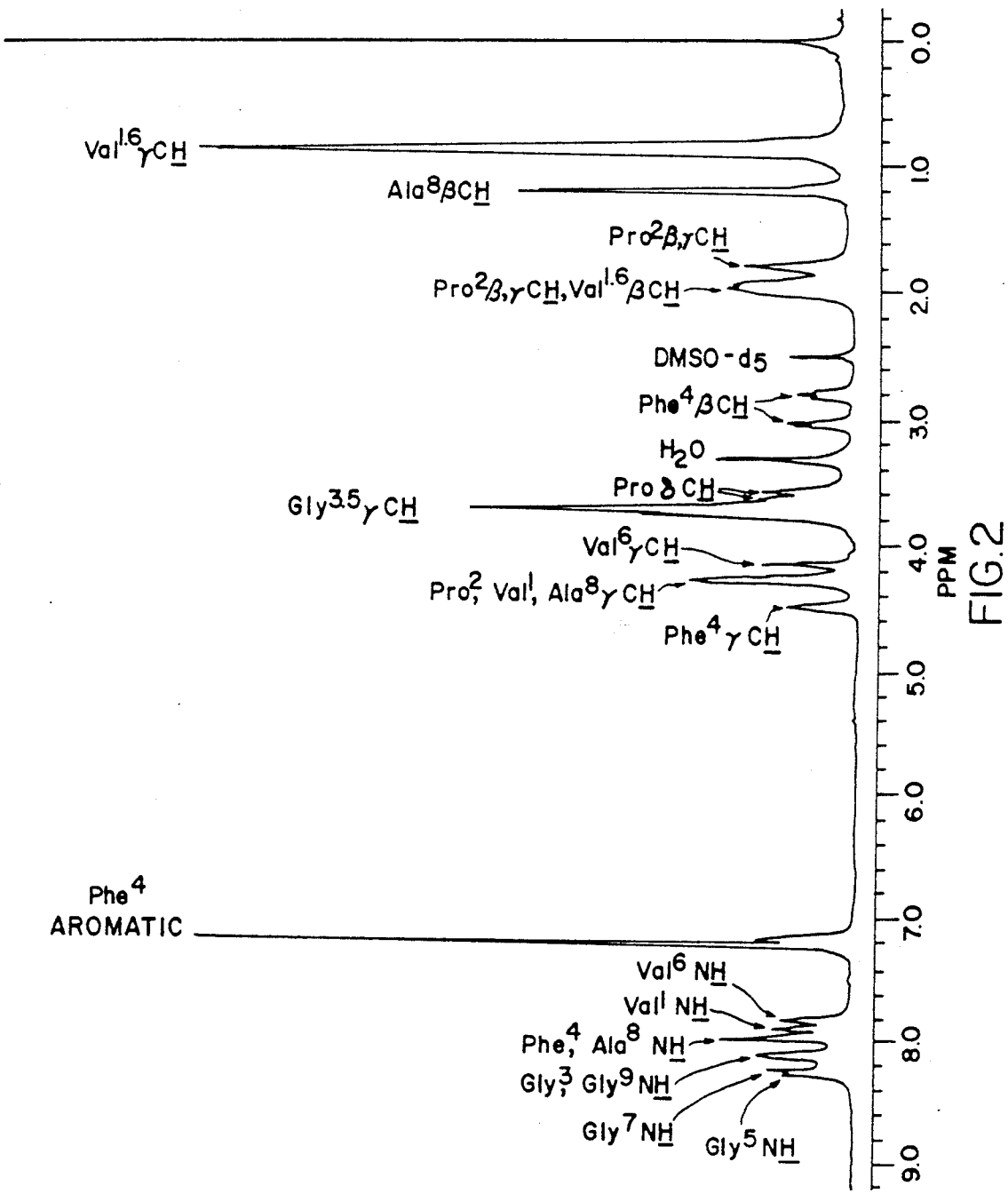
FIG. 2 represents a 400 MHz $^1$H-NMR spectrum of poly(VPGFGVGAG) which was obtained by dissolving 20 mg of sample 0.4 ml of DMSO-$d_6$. 64 scans were accumulated with 8K data points and spectral width of 4 KHz.

The carbon-13 and proton NMR data of FIGS. 1 and 2 evidence the obtainment of the polynonapeptide sequence poly(VPGFGVGAG). The sequence was also confirmed using both correlation and nuclear Overhauser enhancement spectroscopy.

When greater than 50,000 molecular weight polynonapeptide is prepared by means of equilibrium dialysis with a 50 kD cut-off dialysis membrane, the material is found to be solubilized below 5° C. in water. As seen from the temperature profiles of turbidity formation (TP$\tau$) in FIG. 3, the midpoint of the TP$\tau$ for a concentration of a 40 mg/ml solution is about 8° C. whereas for a 1 mg/ml solution, the midpoint is raised only to about 11° C. The slope of the profile has decreased on dilution consistent with a cooperative nature to the aggregational process which has been extensively demonstrated to be an inverse temperature transition for poly(VPGVG).

Figure 4:
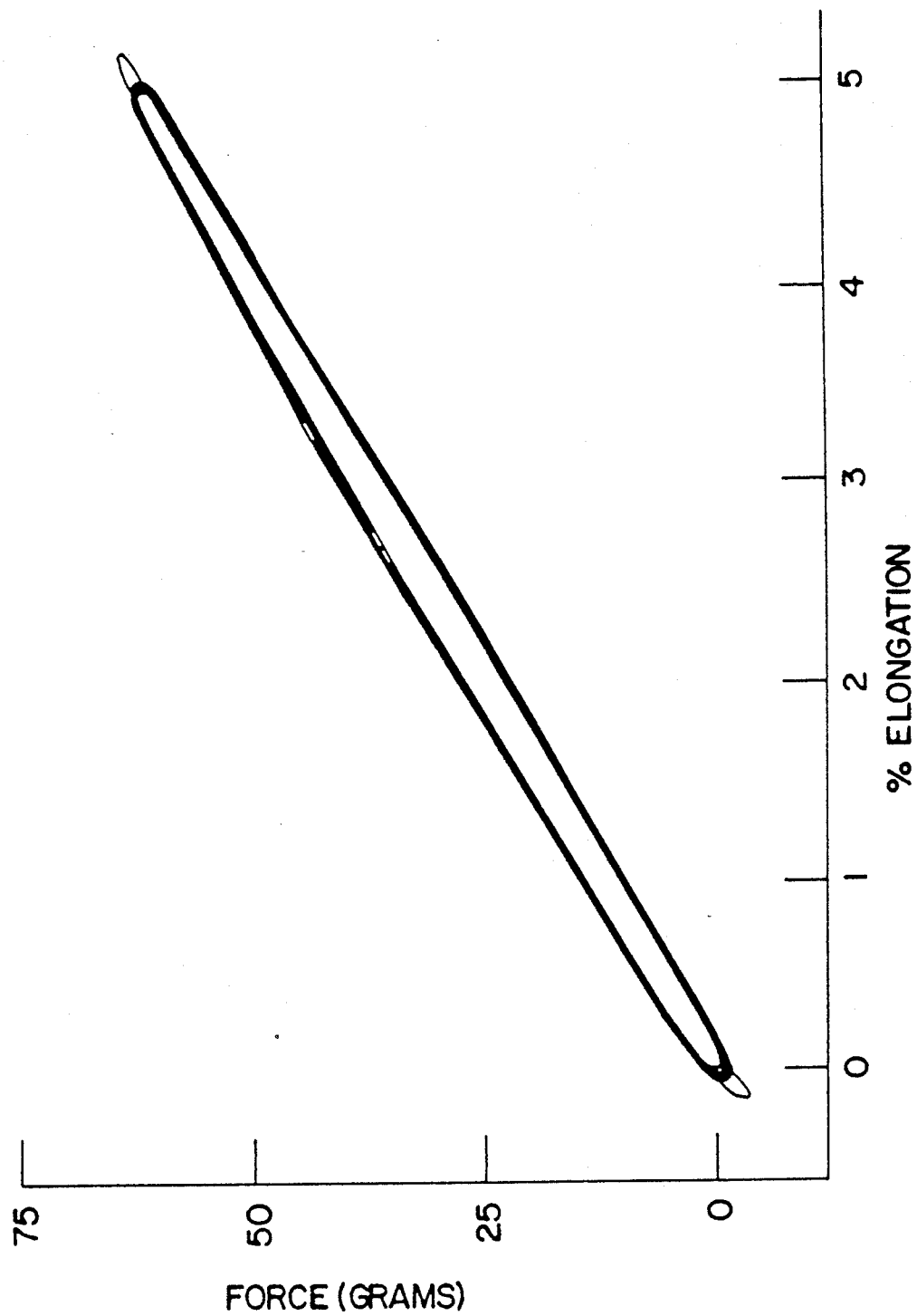
FIG. 4 illustrates stress/strain curves (force plotted as a function of percent extension) of X$^{20}$-polynonapeptide showing reproducible cycling with a regular amount of hysteresis when the peptide is repeatedly stretched and relaxed.

The stress/strain data for two $\gamma$-irradiation cross-linked samples of $X^{20}$-PNP are given in FIG. 4. After the initial cycle (not shown), there is a readily reproducible curve obtained with a regular amount of hysteresis. The elastic modulus at 4% extension was approximately 6 to $7 \times 10^7$ dynes/cm$^2$ for the sample cycled at 5% extensions. Cyclic extensions up to >60% have been demonstrated. When a 25 Mrad cross-linking dose was used, elastic moduli of $10^8$ dynes/cm$^2$ have been obtained. This elastic modulus is two orders of magnitude greater than that obtained with similarly treated poly (VPGVG). Thus, the present polynonapeptide sequences afford bioelastomers having excellent elastic properties.

The present polynonapeptides also exhibit chemotaxis toward fibroblasts and endothelial cells. Chemotaxis is the vectorial translocation of cells in response to an increasing chemical gradient. Thus, with present polynonapeptide, it is now possible to prepare elastomeric polypeptide biomaterials which, with the appropriate mix of PPP and PTP, can be made to match vascular wall compliance. Such chemotactic sequences within the prepared biomaterials support the development of an endothelial lining in the case of vascular walls, or the invasion of fibroblasts in the case of a ligament or a scaffolding for a ligament.

The chemotaxis of the present polynonapeptide towards fibroblasts and endothelial cells can be determined and verified by the well known checkerboard assay of Zigmond and Hirsch. See S. H. Zigmond and J. G. Hirsch, "Leukocyte Locomotion and Chemotaxis: New Methods for Evaluation and Demonstration of a Cell Derived Chemotactic Factor", J. Exp. Med. 137, 387–410 (1973). Checkerboard analysis of AGVPGFGVG and GFGVGAGVP sequences with fibroblasts using the procedure as described above afforded the following results which are represented graphically in Tables I and II.

TABLE I

Checkerboard Analysis of AGVPGFGVG with Fibroblasts

| | | Peptide concentration above filters (M) | | | |
|---|---|---|---|---|---|
| | | 0 | $10^{-10}$ | $10^{-9}$ | $10^{-8}$ |
| Peptide conc. | 0 | (10) 0 ± 1.3 | −2 ± 1.1 | −2 ± 0.5 | −3 ± 0.9 |
| below filters | $10^{-10}$ | 6 ± 1.3 | −3 ± 1.0 | −4 ± 0.8 | 2 ± 1.8 |
| (M) | $10^{-9}$ | 25 ± 1.6 | 3 ± 1.7 | −4 ± 0.6 | −2 ± 1.1 |
| | $10^{-8}$ | 9 ± 2.3 | 5 ± 1.6 | 5 ± 1.2 | −2 ± 1.1 |

Results are expressed as mean ± S.E.M. where n = 15. Positive control, PDGF at 60 μg/ml = 21.

TABLE II

Checkerboard Analysis of GFGVGAGVP with Fibroblasts

| | | Peptide concentration above filters (M) | | | |
|---|---|---|---|---|---|
| | | 0 | $10^{-10}$ | $10^{-9}$ | $10^{-8}$ |
| Peptide conc. | 0 | (9) 0 ± 1.0 | −1 ± 1.0 | −3 ± 1.2 | −2 ± 1.4 |
| below filters | $10^{-10}$ | 13 ± 1.6 | −1 ± 0.8 | −3 ± 0.7 | −1 ± 0.8 |
| (M) | $10^{-9}$ | 45 ± 3.4 | 7 ± 1.8 | −2 ± 1.0 | −1 ± 1.1 |
| | $10^{-8}$ | 21 ± 1.5 | 12 ± 1.6 | 7 ± 1.5 | 0 ± 1.50 |

Results are expressed as mean ± S.E.M. where n = 15. Positive control, PDGF at 30 μg/ml = 59.

The various polynonapeptide permutations of the present invention, in order to exhibit chemotactic behavior generally preferably have a nonapeptide sequence concentration in the range of $10^{-5}$ to $10^{-12}$ M.

However, for both endothelial cell and fibroblast chemotaxis, it is more preferred that the present nonapeptide sequences have a concentration releaseable form the elastomeric polypeptide in the range of $10^{-7}$ to 10hu $-10$ M.

The nonapeptide or octameric sequences as described above, either as unit or repeating sequences may be either chemically bonded, i.e., covalently bonded within an elastomeric matrix or the nonapeptide, or octameric sequences described above may be "doped", i.e., physically intermingled, within the elastomeric matrix. By either approach, the peptide sequence of interest is gradually released from the elastomeric matrix.

In addition to all of the sequence modifications described above which are used to modify the temperature of the inverse temperature transition, it is also possible to modify the nonapeptide sequences disclosed herein. In particular, it is possible to modify the $\alpha$, $\delta$ or $\pi$ positions, i.e., positions $i+3$ and $(i+3)'$, with a residue such as Glu. However, other modifications may be made at the $\alpha$, $\delta$, or $\pi$ positions in accordance with the above description with respect to PPP and PTP.

All of the polypeptide sequences described herein must, of necessity, be cross-linked in order to be utilized as elastomeric materials. Specific procedures which may be used to effect cross-linking and various sidechain moieties and chemical agents which may be used therefore have been described in some of the U.S. patents already incorporated herein by reference.

In accordance with another important aspect of the present invention, the nonapeptide and polynonapeptide sequences disclosed herein may be advantageously used in the construction of vascular prosthetic materials and ligaments. This will now be discussed in detail.

The present nonapeptide and polynonapeptide sequences can be used in conjunction with other elastomeric polypeptides as described in copending application Ser. No. 07/184,873, which is incorporated herein by reference in the entirety in the construction of vascular prosthetic materials. These elastomeric polypeptides can be constructed to match the compliance of small vessels in mammals, particularly humans.

In the most basic form, an elastomeric vessel may be prepared which contains a single-layer wall containing the nonapeptide or polynonapeptide sequences of the present invention. However, the elastomeric vessel may be constructed to have a wall with at least three layers, or even more.

In perhaps the most fundamental form, the elastomeric prostheses of the present invention consists of an elastomeric tube or vessel containing predominantly repeating units of elastin pentapeptide (VPGVG), with the remainder being the repeating hexapeptide (VAPGVG) and/or the nonapeptide or the polynonapeptide of the present invention. Thus, the formula of the bulk matrix may be generally written as A. $[(VPGVG)_m—(\alpha\beta\gamma\delta\epsilon\theta\lambda\pi\rho)_n]_l$
B. $[(VPGVG)_m—(\alpha\beta\gamma\delta\epsilon\theta\lambda\pi\rho)_n—(VAPGVG)_o]_l$
C. $[(VPGVG)_m—(VAPGVG)_o—(\alpha\beta\gamma\delta\epsilon\theta\lambda\pi\rho)_n]_l$ wherein m may have a value of 0 to about 20, n may have a value of from 2 to 20, preferably 3 to 15 for both m and n, and o has a value of from about 0 to 20, preferably 3 to 9. l has a value such that upon $\gamma$-irradiation the bulk matrix will have an appropriate elastic modulus. Generally, a molecular weight in the range of 10,000–50,000 daltons will be adequate as a minimal molecular weight. However, molecular weights of up to about 1,000,000 daltons may be used.

The elastomeric prostheses may be constructed so as to have one or more layers, each layer having a specialized function. For example, in accordance with the present invention as elastomeric vessel may be designed to contain one or more layers having cell attachment sequences for endothethial cells or smooth muscle cells. Alternatively or additionally, a layer may be designed for attachment to surrounding connective tissue and for selective interactions with fibroblasts.

Elastomeric prostheses may also be constructed which contain several layers each with a particular and different function. For example, a three-layered elastomeric vessel may be constructed, the vessel wall of which contains (1) an intimal-inner layer specialized for cell attachment of endothelial cells, (2) a medial-middle layer specialized for cell attachment of smooth muscle cells, and (3) an adventitial-outer layer specialized for attachment to surrounding connective tissue and for cell attachment of fibroblasts. The particular elastomeric components for each of these layers and their properties will now be discussed.

PROPERTIES OF THE ELASTOMERIC PROSTHESIS COMPONENTS

A basic elastomeric polypeptide is the polypentapeptide, (Val-Pro-Gly-Val-Gly)$_n$ abbreviated (VPGVG)$_n$ or simply PPP. A viscoelastic state of the PPP which is approximately 40% peptide and 60% water by weight may be $\gamma$-irradiation cross-linked to form an elastomeric matrix. The elastic modulus (Young's modulus, YM) obtained on preparation of the cross-linked PPP matrix is dependent on the $\gamma$-irradiation cross-linking dose. Stress-strain data obtained on a band of 20 Mrad cross-linked polypentapeptide ($X^{20}$-PPP) for a sequence of cycles at 10% increments up to 90% illustrates the low degree of hysteresis for these initial extensions. For such a sample, rupture occurs on approaching 100% extension, though extensions of greater than 200% are routinely obtained when the sample is prepared without vacuolization. The material is significantly strengthened and is given more body for ease of handling by compounding with a polyhexapeptide, (VAPGVG)$_o$, PHP. A series of stress/strain curves for the $X^{20}$-(PHP:PPP, 1:6) taken at larger percent increments illustrates the extent of hysteresis and a rupture of this sample on approaching 200% extension. When the sequential multicomponent models are prepared, i.e., $[(VPGVG)_m—(VAPGVG)_o]_l$, and cross-linked properties yet more favorable will be obtained than simply mixing PHP and PPP in parallel.

To more clearly illustrate the advantageous properties of the present elastomeric prostheses, comparison with natural vessels is noted. For the dog femoral artery, there is an irreversible hysteresis for extensions above 30% presumably because collagen fibers came into tension and rupture. In an elastomeric vascular prosthesis, the purpose of which is to provide a scaffolding for regeneration of the natural artery, a low extension elasticity is required. Notably, the basic synthetic elastomeric matrices have the requisite property which for $X^{20}$-PPP falls between the values for the internal mammary and femoral arteries. This property can be fine tuned to match well the stress/strain characteristics in the 0 to 30% extension range. It, of course, is to be appreciated that the radial dilatations and changes in length in situ normally are less than 20% with the special exception of the pulmonary artery of man where the radial dilatation is 60 to 70% and the static elastic moduli ($Ep = \Delta PR/\Delta R$) vary from about $0.4 \times 10^6$ dynes/cm$^2$ for the carotid artery of man to about $3 \times 10^6$ dynes/cm$^2$ for the femoral artery. Also, the active contractile force developed by vascular muscle is in the range of 2 to $3 \times 10^6$ dynes/cm$^2$ for the carotid and pulmonary arteries. These elastic properties of vascular wall are attainable with the described elastomeric polypeptide vascular materials.

Preliminary stress/strain studies have also been used to assess suture pull-out characteristics. Comparison has been made with the internal mammary artery of dog where single suture pull-out occurred at a stress of 11 grams/mm$^2$; using the same Prolene TM suture, value for $X^{20}$-(PHP:PPP, 1:6) occurred at 4.3 grams/mm$^2$. This was with a sample that was formed before methods for improving uniformity of the PHP and PPP mix and while vacuolization was yet a significant factor. It is expected that suture pull-out values similar to those of the internal mammary artery can be obtained for the synthetic material.

The polypentapeptide when formed as an elastomeric matrix results in a very interesting biomaterial. For vascular wall, however, a matrix of greater strength and easier handling characteristics could be desired. This has been achieved by combining polypentapeptide (PPP) with polyhexapeptide (PHP) to obtain a matrix. The more gelatinous-like $X^{20}$-PPP (20 Mrad cross-linked polypentapeptide matrix) on addition of PHP becomes more teflon-like. One approach is making a section of synthetic elastomeric tube is to dissolve PPP and PHP in water at low temperature in a suitable tube. On raising the temperature, a coacervate phase is formed and the excess water is removed. A pestle can then be inserted into the viscoelastic phase which flows into and fills the channel in the pestle. On $\gamma$-irradiation cross-linking, the pestle is removed from the tube and the cross-linked matrix is removed from the pestle to obtain an elastomeric tube.

The stress/strain curves of the composite PHP/PPP matrix are temperature dependent. The elastic modulus is seen to increase with temperature and for $X^{20}$-(PHP:PPP, 1:6) the elastic modulus is in the range of 2 to $4 \times 10^6$ dynes/cm$^2$ near physiological temperatures. Above 55° C., the matrix begins to destructure as reflected by the loss of elastic modulus. Accordingly, a small caliber vessel (e.g., the 4.8 mm ID tube shown) can be formed for consideration as a synthetic elastomeric polypeptide vascular material and it contains within it polypeptide that has been found to be chemotactic toward vascular wall cells.

VASCULAR WALL LAYERING

As noted above, the properties of the sequential polypeptides of elastin may be varied considerably and may be used in linear or cross-linked combination in a single layer of material or various layers, each having a different composition, which may be combined advantageously.

The present invention will now be further illustrated by the following example which is provided for purposes of illustration only and is not intended to limit the present invention.

EXAMPLE

Formation of an Intimal Layer

The intimal layer may contain PPP, the polynonapeptide (PNP) or composition A as indicated above which is $[(VPGVG)_m—(\alpha\beta\gamma\delta\epsilon\theta\lambda\pi\rho)_n]_l$, where m, n and l are as defined. Also, cell attachment sequences for endothelial cells may also be included within the primary structure. For example, cell attachment sequence concentrations of up to about 1 sequence per 100 matrix residues are suitably used. Preferably, however, one or more of the polynonapeptides are used in this layer.

The polypentapeptide in the precross-linked state at 37° C. is a sticky material which adheres to all but hydrophobic surfaces. The 37° C. state is 38% peptide and 62% water by weight, but on drying, it hardens and becomes glass-like. Accordingly, it is a simple process to apply a thin layer of polypentapeptide on a rotating pestle; the PPP or any variant thereof as described previously, would contain, within its primary structure, cell attachment sequences for endothelial cells and as well could contain dissolved within the viscoelastic mass an appropriate concentration of chemotactic peptides for endothelial cells. Additionally, as noted previously, the composition of the polypentapeptide can be varied to compensate for the effect of adding cell attachment sequences and chemotactic peptides and the temperature of the inverse temperature. While the pestle rotates, the sample dries forming a layer of dried glue of desired thickness on the pestle.

Addition of a Medial Layer: The pestle with the dried intimal layer can be inserted into the tube of desired diameter which, in its bottom, contains the viscoelastic mass that is to be the medial layer. This would be a PHP/PPP/PNP or PPP/PNP coacervate at its 37° C. water composition. Once the pestle is inserted, the coacervate fills the space between the intimal layer and the tube wall. The intimal layer slowly hydrates but does not lose its identity due to the extremely slow diffusion of the high molecular weight polypeptides at compositions of 40% peptide by weight. When an additional layer is desired then a lower cross-linking dose, say 10 Mrad would result in an insoluble matrix that could be further layered.

Generally, for the medial layer, elastomeric matrices are used of the formula:

$$[(VPGVG)_m - (\alpha\beta\gamma\delta\epsilon\theta\lambda\pi\rho)_n]_l$$

$$[(VPGVG)_m - (\alpha\beta\gamma\delta\epsilon\theta\lambda\pi\rho)_n - (VAPGVG)_o]_l$$

$$[(VPGVG)_m - (VAPGVG)_o - (\alpha\beta\gamma\delta\epsilon\theta\lambda\pi\rho)_n]_l$$

Generally, in the above formulae, m may have a value of from about 0 to about 20, preferably 3 to 15, n may have a value of from 2 to about 20, preferably 3 to 15, and o has a value of 2 to about 20, preferably 3 to 9.0 is defined previously. However, l can have a high value corresponding to a value of (m+n) of as high as 5,000.

In addition, to being the primary structural component of the vascular wall the medial layer is to be specialized for smooth muscle cells by inclusion of the appropriate cell attachment and chemotactic peptide sequences.

As noted above, a dose of $\gamma$-irradiation is used which is, generally, the lowest possible dose required to match the compliance of the vascular wall. However, doses in excess of 30–40 Mrad are not generally used.

Addition of an Adventitial Layer: Using a larger tube, the cylinder with intimal and medial layers surrounding the pestle at 37° C. is inserted into a larger tube in which a lysine containing PPP coacervate has been placed. This material then flows around the medial layer to form a third layer. On exposing this tube to another 10 Mrad, the inner layers will have received the desire 20 Mrad and an outer, looser layer will have been added. As the lysine-containing polypentapeptide or polytetrapeptide is a substrate for the extracellular enzyme, lysyl oxidase, the potential exists for the adventitial layer to become covalently cross-linked to the extracellular matrix surrounding the implant site. This is because oxidation of lysine by lysyl oxidase to form the aldehyde is the natural mechanism for cross-linking in the extracellular matrix.

As noted, any additional method of chemical cross-linking using cross-linking units capable of being cross-linked by lysyl oxidase may be used as described in U.S. Pat No. 4,589,882. For the intimal and adventitial layers, the sequences as pentameters (VPGVG), tetramers (VPGG) or hexamers (VAPGVG) may be added in the desired ratio and then polymerization is carried out such that the incorporation along the sequence is random to obtain a polymer of greater than 50 kD. For the medial layer, the sequences may be incorporated as desired in a single long sequence of the order of 100 residues, and then this unit is polymerized to a greater molecular weight. As an example of a medial layer, can be mentioned a layer which is obtained by appropriately mixing polynonapeptide and polypentapeptide, each of greater than 50 kD, which are cross-linked by γ-irradiation.

The adventitial layer may also contain cell attachment sequences for fibroblasts such as the sequences GRGDSP or RGD, using the standard one letter amino acid abbreviation. Concentrations of up to 1 cell attachment sequence per 100 matrix residues may be used.

Further, at the junction between the intimal and medial layers or layered within the medial matrix or at the outer surface of the medial layer, can be included a porous layer to facilitate migration of smooth muscle cells. This can be achieved by addition of a fine coral or sized particulate carbonate powder to a semi-dry, tacky surface of the coated pestle at any desired radius as long as the γ-irradiation dose is 10 Mrad or less. On drying, the treated pestle with its layers would be introduced into a tube of desired diameter with the PHP/PPP/PNP or PPP/PNP viscoelastic coacervate of the proper volumn in the bottom. On completing the 20 to 25 Mrad dose, the synthetic tube could be removed and treated with acid of sufficient strength to dissolve the carbonates but not of a strength to hydrolyze the peptide.

Additionally, it is noted that instead of using —(VPGVG)— in the basic sequential polypeptide, it is also possible to use generally a pentapeptide of the formula —($R_1PR_2R_3G$)— as already defined previously. Similarly, instead of using —(VAPGVG)— in the basic sequential polypeptide, the variations described previously may also be utilized.

STIMULATION OF CELLS ON THE SURFACE OF ELASTOMERIC MATRICES

The elastomeric materials described herein may be advantageously used as vascular prostheses for the following additional reason. In particular, when cells, such as smooth muscle cells and/or endothelial cells, are attached to the surface of elastomeric matrices and subjected to stretch/relaxation cycles, it is found that the cells are stimulated to produce the macromolecules which make up the vascular wall. In other words, the cells are stimulated to produce their own vascular wall.

The above aspect of the present invention is, in part, based upon the earlier work of Glagov who demonstrated that elastic substrates might be used to stimulate cell synthesis of matrix components. See *Exp. Cell Research,* 109, 285–298 (1977); Science, 191, 75–477 (1976); and Circ. Res., 14, 400–413 (1964) by Glagov et al. However, none of this work was conducted with the present elastomeric materials.

Further, the biodegradability and biocompatibility of the present vascular prostheses also appear to be advantageous in that it has been demonstrated that compliance and biodegradation of vascular grafts stimulates the regeneration of elastic laminae in neoarterial tissue. See *Cell Tissue Res.* 242, 569–578 (1985), by van der Lei et al. Thus, the present vascular prostheses have the advantageous effect of stimulating the synthesis of cell matrix components, such as collagen and new elastic fibers, to thereby regenerate vascular walls.

LIGAMENT CONSTRUCTION

In addition to constructing vascular prosthesis, the elastomeric polypeptides can be advantageously used in the construction of artificial ligaments.

Although any of the above-described elastomeric materials can be utilized, in conjunction with the present nonapeptide and polynonapeptide sequences, in the construction of artificial ligaments, the artificial ligaments of the present invention are most advantageously constructed from any one of the following three compositions:

A. $[(VPGVG)_m-(\alpha\beta\gamma\delta\epsilon\theta\lambda\pi\rho)_n]_l$ or
B. $[(VPGVG)_m-(\alpha\beta\gamma\delta\epsilon\theta\lambda\pi\rho)_n-(VAPGVG)_o]_l$ or
C. $[(VPGVG)_m-(VAPGVG)_o-(\alpha\beta\gamma\delta\epsilon\theta\lambda\pi\rho)_n]_l$ wherein m may have a value of 0 to about 20, preferably 3 to 15, n may have a value of from 2 to about 20, preferably 3 to 15, and o has a value of from about 2 to about 20, preferably 3 to 9, and l has a value such that upon γ-irradiation the bulk matrix will have an increased elastic modulus.

Generally, however, a molecular weight in the range of 10,000–50,000 daltons will be adequate as a minimal molecular weight. However, a molecular weight of up to about 1,000,000 daltons may be used.

The artificial ligaments of the present invention may also contain cell attachment sequences for fibroblasts such as the sequences GRGDSP or RGD. These same cell attachment sequences may also be used for the vascular prosthesis described above. Further, as an example of a chemotactic peptide which may be used with either the described vascular prosthesis or artificial ligament is the sequence ⫟VGVAPG⫠ or permutations thereof such as ⫟GVGVAP⫠ or ⫟PGVGVA⫠. Concentrations of up to 1 cell attachment sequence per 100 matrix residues may be used.

Although the artificial ligaments can be constructed from any of the above-mentioned elastomeric materials, it is preferred that a mixture of one or more of the present polynonapeptides be incorporated in the elastomeric matrix. For example, it is advantageous to construct a ligament from a mixture of a polynonapeptide and a polyhexapeptide (PHP) to afford both high elastic modules and mechanical strength. The proportions of each may be 1 to 99 molar % to 99 to 1 molar % with the precise combination being determined by the elasticity and mechanical strength desired.

The artifical ligament of the present invention may be utilized in accordance with techniques described in U.S. Pat. Nos. 4,773,910, 4,731,084, 4,642,119, 4,246,660 and 4,149,277; all of which are incorporated herein in the entirety.

It should be emphasized, however, that the present elastomeric polypeptide materials are used as a temporary functional scaffolding for ligament reconstruction wherein cellular in growth and elaboration of natural ligaments is an integral aspect of the present invention. As such, one skilled in the art would easily be able to utilize the present elastomeric polypeptide materials in accordance with any or all of the incorporated U.S. patents in fashioning ligaments.

The vascular prosthesis and artificial ligaments of the present invention are constructed of elastomeric materials which are all capable of reversibly contracting and relaxing by an inverse temperature transition. These elastomeric materials are preferably substantially cross-linked. The vascular prosthesis is preferably in the form of a vessel suitable for use as a portion of an artery, vein or lymphatic vessel.

The elastomeric matrices of which the vascular prosthesis and artificial ligaments are constructed are generally made of repeating units of elastomeric tetrapeptide and pentapeptide repeating units and units thereof modified by hexapeptide units and mixtures thereof, wherein the repeating units contain amino acid residues, i.e., peptide-forming residues, of hydrophobic amino acid residues and glycine residues, and wherein the repeating units exist in a conformation having a $\beta$-turn. Such matrices may, for example, be used as moieties A and B defined above. Of course, the above generalized compositions are modified as specifically described above in order to contain the disclosed polynonapeptide sequences, or the specific compositions disclosed for the various vascular prosthetic layers.

Having fully described the present invention, it will be apparent to one skilled in the art that many changes and modifications may be made to the same without departing from either the spirit or scope thereof.

What is claimed as new and desired to be secured by Letters Patent of the United States is:

1. A polynonapeptide of the formula:

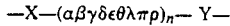

$$-X-(\alpha\beta\gamma\delta\epsilon\theta\lambda\pi\rho)_n-Y-$$

wherein:
α is a peptide-forming residue of L-Valine or another peptide-forming residue capable of functioning in position i of a $\beta$-turn in a polypeptide;
β is a peptide-forming residue of L-Proline or another peptide-forming residue capable of functioning in position i+1 of a $\beta$-turn in a polypeptide;
γ is a peptide-forming residue of L-Glycine or another peptide-forming residue capable of functioning in position i+2 of a $\beta$-turn in a polypeptide;
δ is a peptide-forming residue of L-Phenylalanine or another peptide-forming residue capable of functioning in position i+3 of a $\beta$-turn in a polypeptide; ε is a peptide-forming residue of Glycine or D-Alanine, when functioning as position i' of a subsequent $\beta$-turn in a polypeptide when δ is as defined, or ε is as defined for α when δ is Glycine or D-Alanine;

θ is a peptide-forming residue of L-Valine or another peptide-forming residue as defined above for α, or when functioning as position (i+1)' of a subsequent $\beta$-turn in a polypeptide, θ is a peptideforming residue as defined above for β;
λ is a peptide-forming residue of Glycine, D-Alanine or another peptide-forming residue as defined for γ, when functioning as position (i+2)' of a subsequent $\beta$-turn in a polypeptide;
π is a peptide-forming residue of L-Alanine or another peptide-forming residue as defined for δ, when functioning as position (i+3)' in a subsequent $\beta$-turn in a polypeptide, or a direct bond; and
ρ is a peptide-forming residue of Glycine, or D-Alanine; another peptide-forming residue as defined for δ, when
wherein X is $\beta\gamma\delta\epsilon\theta\lambda\pi\rho$, $\gamma\delta\epsilon\theta\lambda\pi\rho$, $\delta\epsilon\lambda\pi\rho$, $\epsilon\theta\lambda\pi\rho$, $\theta\lambda\pi\rho$, $\lambda\pi\rho$, $\pi\rho$, $\rho$ or a direct bond; Y is $\alpha\beta\gamma\delta\epsilon\theta\lambda\pi$, $\alpha\beta\gamma\delta\epsilon\theta\lambda$, $\alpha\beta\gamma\delta\epsilon\theta$, $\alpha\beta\gamma\epsilon$, $\alpha\beta\gamma\delta$, $\alpha\beta\gamma$, $\alpha\beta$, $\alpha$ or a direct bond; and n has a value of 1 to about 5,000; and with the proviso that no more than three of residues $\epsilon$, $\theta$, $\lambda$, $\pi$ and $\rho$ are simultaneously a peptide-forming residue of Glycine.

2. The polypeptide of claim 1, wherein
α is selected from the group consisting of peptide-forming residues of L-valine, L-isoleucine, L-Leucine, L-phenylalanine, L-tryptophan and L-tryosine;
β is selected from the group consisting of peptide-forming residues of L-proline, L-valine, L-isoleucine, L-leucine, L-phenylalanine, L-tryptophan and L-tyrosine;
γ is selected from the group consisting of peptide-forming glycine, L-alanine, D-alanine, D-valine, D-isoleucine, D-leucine, D-phenylalanine, D-tryptophan and D-tyrosine;
δ is selected from the group consisting of peptide-forming residues of L-valine, L-isoleucine, L-leucine, L-phenylalanine, L-tryptophan and L-tyrosine; or is selected from the group consisting of Glycine and D-Alanine;
ε is selected from the group consisting of peptide-forming residues of glycine and D-alanine, when δ is L-valine, L-isoleucine, L-leucine, L-phenylalanine, L-tryptophan and L-tyrosine; or ε is as defined for α when γ is glycine or D-alanine;
θ is selected from the group consisting of peptide-forming residues of L-valine, L-isoleucine, L-leucine, L-phenylalanine, L-tryptophan and L-tyrosine; or a peptide-forming residue of L-proline;
λ is selected from the group consisting of peptide-forming residues of glycine, D-alanine, L-valine, L-isoleucine, L-leucine, L-phenylalanine, L-tryptophan and L-tyrosine;
π is selected from the group consisting of L-alanine, L-valine, L-isoleucine, L-leucine, L-phenylalanine, L-tryptophan and L-tyrosine, or is a direct bond; and
ρ is selected from the group consisting of glycine, and D-alanine.

3. The polynonapeptide of claim 2, wherein
α is a peptide-forming residue of L-valine;
β is a peptide-forming residue of L-proline;
γ is a peptide-forming residue of glycine;
δ is a peptide-forming residue of L-phenylalanine or L-leucine;
ε is a peptide-forming residue of glycine;
θ is a peptide-forming residue of L-valine;

λ is a peptide-forming residue of glycine;
π is a peptide-forming residue of L-valine or L-alanine or a direct bond;
ρ is a peptide-forming residue of glycine.

4. The polynonapeptide of claim 3, wherein δ is a peptide-forming residue of L-phenylalanine and π is a peptideforming residue of glycine.

5. An elastomeric polypeptide of the formula:

$$-(A-(\alpha\beta\gamma\delta\epsilon\theta\lambda\pi\rho)-_nB)-_m$$

wherein
- α is a peptide-forming residue of L-Valine or another peptide-forming residue capable of functioning in position i of a β-turn in a polypeptide;
- β is a peptide-forming residue of L-Proline or another peptide-forming residue capable of functioning in position i+1 of a β-turn in a polypeptide;
- γ is a peptide-forming residue of L-Glycine or another peptide-forming residue capable of functioning in position i+2 of a β-turn in a polypeptide;
- δ is a peptide-forming residue of L-Phenylalanine or another peptide-forming residue capable of functioning in position i+3 of a β-turn in a polypeptide;
- ε is a peptide-forming residue of Glycine or D-Alanine, when functioning as position i' of a subsequent β-turn in a polypeptide when δ is as defined, or ε is as defined for α when δ is glycine or D-alanine;
- θ is a peptide-forming residue of L-Valine, L-Alanine or another peptide-forming residue as defined above for α, or when functioning as position (i+1)' of a subsequent β-turn in a polypeptide, θ is a peptide-forming residue as defined above for β;
- λ is a peptide-forming residue of Glycine, D-Alanine or another peptide-forming residue as defined for γ, when functioning as position (i+2)' of a subsequent β-turn in a polypeptide;
- π is a peptide-forming residue of L-Alanine or another peptide-forming residue as defined for δ when functioning as position (i+3)' in a subsequent β-turn in a polypeptide, or a direct bond; and
- ρ is a peptide-forming residue of Glycine or D-alanine;

wherein X is $\beta\gamma\delta\epsilon\theta\lambda\pi\rho$, $\gamma\delta\epsilon\theta\lambda\pi\rho$, $\epsilon\theta\lambda\pi\rho$, $\theta\lambda\pi\rho$, $\lambda\pi\rho$, $\pi\rho$, $\pi$ or a direct bond; Y is $\alpha\beta\gamma\delta\epsilon\theta\lambda\pi$, $\alpha\beta\gamma\delta\epsilon\theta\lambda$, $\alpha\beta\gamma\delta\epsilon\theta$, $\alpha\beta\gamma\delta\epsilon$, $\alpha\beta\gamma\delta$, $\alpha\beta\gamma$, $\alpha\beta$, $\alpha$ or a direct bond; and n has a value of 1 to about 5,000; and with the proviso that no more than three of residues ε, θ, λ, π and ρ are simultaneously a peptide-forming residue of Glycine; and wherein each of A and B, which are the same or different, represent a moiety which is capable of modulating elastomeric force by an inverse temperature transition; and m and n each have a value of from 1 to about 5,000.

6. The elastomeric polypeptide of claim 5, wherein said moieties A and B are selected from the group consisting of $-(APGVGV)-_m$ $-(VPGVG)-_m$, $-(IPGVG)-_m$, $-(VPGAG)-_m$, $-(VPGG)-_m$, $-(IPGG)-_m$ and $-(FPGG)-_m$ wherein:
V is a peptide-forming residue of L-valine;
P is a peptide-forming residue of L-proline;
G is a peptide-forming residue of glycine;
I is a peptide-forming residue of isoleucine;
A is a peptide-forming residue of L-alanine; and
F is a peptide-forming residue of L-phenylalanine;
and m has a value of from 1 to about 5,000.

7. The elastomeric polypeptide of claim 5, wherein said moieties A and B, which are the same or different, are each an elastomeric material selected from the group consisting of elastomeric tetrapeptide and pentapeptide repeating units and units thereof modified by hexapeptide units and mixtures thereof, wherein said repeating units comprise amino acid residues selected from the group consisting of hydrophobic amino acid and glycine residues, and wherein said repeating units exist in a conformation having a β-turn.

8. A vascular prosthetic material comprising at least one layer of a material comprising a polynonapeptide of the formula:

$$-X-(\alpha\beta\gamma\delta\epsilon\theta\lambda\pi\rho)_n-Y-$$

wherein:
- α is a peptide-forming residue of L-valine or another peptide-forming residue capable of functioning in position i of a β-turn in a polypeptide;
- β is a peptide-forming residue of L-Proline or another peptide-forming residue capable of functioning in position i+1 of a β-turn in a polypeptide;
- γ is a peptide-forming residue of L-Glycine or another peptide-forming residue capable of functioning in position i+2 of a β-turn in a polypeptide;
- δ is a peptide-forming residue of L-Phenylalanine or another peptide-forming residue capable of functioning in position i+3 of a β-turn in a polypeptide;
- ε is a peptide-forming residue of Glycine or D-Alanine, when functioning in position i' of a subsequent β-turn polypeptide when δ is as defined, or ε is as defined for α when δ is Glycine or D-Alanine;
- θ is a peptide-forming residue of L-Valine or another peptide-forming residue as defined above for α, or when functioning as position (i+1)' of a subsequent β-turn in a polypeptide, θ is a peptide-forming residue as defined above for β;
- λ is a peptide-forming residue of Glycine, D-Alanine or another peptide-forming residue as defined for γ, when functioning as position (i+2)' of a subsequent β-turn in a polypeptide;
- π is a peptide-forming residue of L-Alanine or another peptide-forming residue as defined for δ, when functioning as position (i+3)' in a subsequent β-turn in a polypeptide, or a direct bond; and
- ρ is a peptide-forming residue of Glycine, or D-Alanine;

wherein X is $\beta\nu\delta\epsilon\theta\lambda\pi\rho$, $\gamma\delta\epsilon\theta\lambda\pi\rho$, $\delta\epsilon\lambda\pi\rho$, $\epsilon\theta\lambda\pi\rho$, $\theta\lambda\pi\rho$, $\lambda\pi\rho$, $\pi\rho$, $\rho$ or a direct bond; Y is $\alpha\beta\gamma\delta\epsilon\theta\lambda\pi$, $\alpha\beta\gamma\delta\epsilon\theta\lambda$, $\alpha\beta\gamma\delta\epsilon\theta$, $\alpha\beta\gamma\delta\epsilon$, $\alpha\beta\gamma\delta$, $\alpha\beta\gamma$, $\alpha\beta$, $\alpha$ or a direct bond; and n has a value of 1 to about 5,000; and with the proviso that no more than three of residues ε, θ, λ, π and ρ are simultaneously a peptide-forming residue of Glycine.

9. The vascular prosthetic material of claim 8, which is in the form of a vessel suitable for use as a portion of an artery, vein or lymphatic vessel.

10. The vascular prosthetic material of claim 8, which is substantially cross-linked.

11. The vascular prosthetic material of claim 8, wherein said at least one layer comprises at least one of the following compositions:

A. $[(VPGVG)_m-(\alpha\beta\gamma\delta\epsilon\theta\lambda\pi\rho)_n)]_l$ or
B. $[(VPGVG)_m-(\alpha\beta\gamma\delta\epsilon\theta\lambda\pi\rho)_n-(VAPGVG)_o]_l$ or
C. $[(VPGVG)_m-VAPGVG)_o-(\alpha\beta\gamma\delta\epsilon\theta\lambda\pi\rho)_n]_l$ wherein:
V is a peptide-forming residue of L-valine;

P is a peptide-forming residue of L-proline;
G is a peptide-forming residue of glycine;
and A is a peptide-forming residue of L-alanine;
and m is in the range of about 0 to 20, n is in the range of 2 to 20; and o is in the range of about 0 to 20, and l has a value such that a minimum molecular weight is obtained in the range of about 10,000 to 50,000 daltons.

12. The vascular prosthetic material of claim 8, which comprises three layers, said vascular prosthetic material comprising:
   (a) an intimal-inner layer, which comprises an elastomeric material selected from the group consisting of one or more of said polynonapeptides and which optionally comprises a component selected from the group consisting of one or more cell attachment sequences for endothelial cells, one or more chemotactic peptides for endothelial cells, and combinations thereof;
   (b) a medial-middle layer, which comprises an elastomeric material and an additional component selected from the group consisting of one or more cell attachment sequences for smooth muscle cells, one or more chemotactic peptides for smooth muscle cells, and combinations thereof; and
   (c) an adventitial-outer layer, which comprises an elastomeric material and an additional component selected from the group consisting of one or more lysine-containing polypentapeptides which render said outer layer capable of being covalently cross-linked to extracellular matrix surrounding said vascular material when implanted and which optionally contains a further component selected from the group consisting of one or more cells attachment sequences for fibroblasts, one or more chemotactic peptides for fibroblasts, and combinations thereof.

13. The vascular prosthetic material of claim 12, wherein said medial-middle layer comprises $[(VPGVG)_m—(\alpha\beta\gamma\delta\epsilon\theta\lambda\pi\rho)_n—(VAPGVG)_o]_l$ or $[(VPGVG)_m—(VAPGVG)_o—(\alpha\beta\gamma\delta\epsilon\theta\lambda\pi\rho)_n]_l$,
wherein V is a peptide-forming residue of L-valine; P is a peptide-forming residue of L-proline; G is a peptide-forming reside of glycine; and A is a peptide-forming residue of L-alanine; and n is an integer in the range of about 0 to 20, n is an integer in the range of about 2 to 20, o is an integer in the range of about 0 to 20, and l has a value such that a minimum molecular weight is obtained in the range of about 10,000 to 50,000 daltons.

14. The vascular prosthetic material of claim 12, wherein said intimal-inner layer comprises:

$$[(VPGVG)_m—(\alpha\beta\gamma\delta\epsilon\theta\lambda\pi\rho)_n]_l$$

or $$—X—(\alpha\beta\gamma\delta\epsilon\theta\lambda\pi\rho)_n—Y—$$

15. The vascular prosthetic material of claim 12, wherein said medial-middle layer comprises an elastomer having the formula:

$$[(VPGVG)_m—(VAPGVG)_o]_l$$

wherein V, P, G, V, G, A, m, n and l are as defined in claim 11.

16. The vascular prosthetic material of claim 12, wherein said adventitial-outer layer comprises an elastomer having the formula:

$$[(VPGKG)_r—(VPGKG)]_s$$

wherein V, P, G, V, G are peptide-forming residues of L-valine, L-proline and glycine; r has a value of about 5 to 30, and s has a value such that a molecular weight of at least 10,000 daltons is obtained.

17. The vascular prosthetic material of claim 16, wherein r has a value of about 10 to 20, and s has a value such that a molecular weight of at least 10,000 to 50,000 daltons is obtained.

18. An artificial ligament having an increased modulus of elasticity, comprising an effective amount of one or more polynonapeptides of the formula:

$$—X—(\alpha\beta\gamma\delta\epsilon\theta\lambda\pi\rho)—_nY—$$

wherein
$\alpha$ is a peptide-forming residue of L-Valine or another peptide forming residue capable of functioning in position i of a $\beta$-turn in a polypeptide;
$\beta$ is a peptide-forming residue of L-Proline or another peptide-forming residue capable of functioning in position i+1 of $\beta$-turn in a polypeptide;
$\gamma$ is a peptide-forming residue of L-Glycine or another peptide-forming residue capable of functioning in position i+2 of a $\beta$-turn in a polypeptide;
$\delta$ is a peptide-forming residue of L-Phenylalanine or another peptide-forming residue capable of functioning in position i+3 of a $\beta$-turn in a polypeptide;
$\epsilon$ is a peptide-forming residue of Glycine or D-Alanine, when functioning as position i' of a subsequent $\beta$-turn in a polypeptide when $\delta$ is as defined or $\epsilon$ is as defined for $\alpha$ when $\delta$ is Glycine or D-Alanine;
$\theta$ is a peptide-forming residue of L-Valine or another peptide-forming residue as defined above for $\alpha$, or when functioning as position (i+1)' of a subsequent $\beta$-turn in a polypeptide, $\theta$ is a peptide forming residue as defined above for $\beta$;
$\lambda$ is a peptide-forming residue of Glycine, D-Alanine or another peptide-forming residue as defined for $\gamma$, when functioning as position (i+2)' of a subsequent $\beta$-turn in a polypeptide;
$\pi$ is a peptide-forming residue of L-Alanine or another peptide-forming residue as defined for $\delta$, when functioning as position (i+3)' in a subsequent $\beta$-turn in a polypeptide, or a direct bond; and
$\rho$ is a peptide-forming residue of Glycine, or D-Alanine;
wherein X is $\beta\gamma\delta\epsilon\theta\lambda\pi\rho$, $\gamma\delta\epsilon\theta\lambda\pi\rho$, $\delta\epsilon\lambda\pi\rho$, $\epsilon\theta\lambda\pi\rho$, $\theta\lambda\pi\rho$, $\lambda\pi\rho$, $\pi\rho$, $\rho$ or a direct bond; Y is $\alpha\beta\gamma\delta\epsilon\theta\lambda\pi$, $\alpha\beta\gamma\delta\epsilon\theta\lambda$, $\alpha\beta\gamma\delta\epsilon\theta$, $\alpha\beta\lambda\delta\epsilon\gamma\delta$, $\alpha\beta\nu$, $\alpha\beta$, $\alpha$ or a direct bond; and n has a value of 1 to about 5,000; and with the proviso that no more than three of residues $\epsilon$, $\theta$, $\lambda$, $\pi$ and $\rho$ are simultaneously a peptide-forming residue of Glycine.

* * * * *